United States Patent
McMahon et al.

(10) Patent No.: US 10,670,700 B2
(45) Date of Patent: Jun. 2, 2020

(54) MULTI SENSOR RADIO FREQUENCY DETECTION

(71) Applicant: RESMED SENSOR TECHNOLOGIES LIMITED, Clonskeagh, Dublin (IE)

(72) Inventors: Stephen McMahon, Dublin (IE); Przemyslaw Szkot, Dublin (IE); Redmond Shouldice, Dublin (IE)

(73) Assignee: ResMed Sensor Technologies Limited (IE)

( * ) Notice: Subject to any disclaimer, the term of this patent is extended or adjusted under 35 U.S.C. 154(b) by 328 days.

(21) Appl. No.: 15/561,769

(22) PCT Filed: Apr. 20, 2016

(86) PCT No.: PCT/EP2016/058791
§ 371 (c)(1),
(2) Date: Sep. 26, 2017

(87) PCT Pub. No.: WO2016/170007
PCT Pub. Date: Oct. 27, 2016

(65) Prior Publication Data
US 2018/0081030 A1      Mar. 22, 2018

Related U.S. Application Data

(60) Provisional application No. 62/207,670, filed on Aug. 20, 2015, provisional application No. 62/149,916, filed on Apr. 20, 2015.

(51) Int. Cl.
*G01S 7/41* (2006.01)
*G01S 7/02* (2006.01)
(Continued)

(52) U.S. Cl.
CPC ............ *G01S 7/415* (2013.01); *A61B 5/0017* (2013.01); *A61B 5/02444* (2013.01);
(Continued)

(58) Field of Classification Search
CPC combination set(s) only.
See application file for complete search history.

(56) References Cited

U.S. PATENT DOCUMENTS 4,197,537 A   4/1980   Follen et al.
4,901,082 A   2/1990   Schreiber et al.
(Continued)

FOREIGN PATENT DOCUMENTS

JP   07333328 A      12/1995
JP   2005283384 A    10/2005
(Continued)

OTHER PUBLICATIONS

Article 94 Communication issued in corresponding EP application No. 16722062.3 dated Nov. 7, 2018.
(Continued)

*Primary Examiner* — Mamadou L Diallo
(74) *Attorney, Agent, or Firm* — Botos Churchill IP Law LLP

(57) ABSTRACT

Radio frequency motion sensors may be configured for operation in a common vicinity so as to reduce interference. In some versions, interference may be reduced by timing and/or frequency synchronization. In some versions, a master radio frequency motion sensor may transmit a first radio frequency (RF) signal. A slave radio frequency motion sensor may determine a second radio frequency signal which minimizes interference with the first RF frequency. In some versions, interference may be reduced with additional transmission adjustments such as pulse width reduction or frequency and/or timing dithering differences. In some ver-
(Continued)

sions, apparatus may be configured with multiple sensors in a configuration to emit the radio frequency signals in different directions to mitigate interference between emitted pulses from the radio frequency motion sensors.

71 Claims, 18 Drawing Sheets

(51) Int. Cl.
| | |
|---|---|
| G01S 13/87 | (2006.01) |
| A61B 5/00 | (2006.01) |
| A61B 5/024 | (2006.01) |
| G01S 13/88 | (2006.01) |
| A61B 5/113 | (2006.01) |
| G01S 13/56 | (2006.01) |
| G01S 13/524 | (2006.01) |
| G01S 7/36 | (2006.01) |
| A61B 5/05 | (2006.01) |
| A61B 5/11 | (2006.01) |
| A61B 5/08 | (2006.01) |

(52) U.S. Cl.
CPC .............. *A61B 5/0507* (2013.01); *A61B 5/08* (2013.01); *A61B 5/11* (2013.01); *A61B 5/113* (2013.01); *A61B 5/7203* (2013.01); *G01S 7/023* (2013.01); *G01S 7/36* (2013.01); *G01S 13/524* (2013.01); *G01S 13/56* (2013.01); *G01S 13/87* (2013.01); *G01S 13/88* (2013.01)

(56) References Cited

U.S. PATENT DOCUMENTS

| | | | | |
|---|---|---|---|---|
| 5,361,070 | A | 11/1994 | McEwan | |
| 5,682,164 | A | 10/1997 | McEwan | |
| 5,966,090 | A | 10/1999 | McEwan | |
| 6,426,716 | B1 | 7/2002 | McEwan | |
| 7,952,515 | B2 * | 5/2011 | McEwan | G01S 13/18 342/118 |
| 2005/0206516 | A1 * | 9/2005 | Tsuji | G01S 7/023 340/522 |
| 2005/0242985 | A1 * | 11/2005 | Ponsford | G01S 7/36 342/59 |
| 2008/0165046 | A1 * | 7/2008 | Fullerton | G01S 7/003 342/21 |
| 2009/0203972 | A1 | 8/2009 | Heneghan et al. | |
| 2010/0214158 | A1 | 8/2010 | McEwan | |
| 2011/0254724 | A1 | 10/2011 | Ricci et al. | |
| 2013/0023285 | A1 * | 1/2013 | Markhovsky | G01S 3/74 455/456.1 |
| 2013/0241766 | A1 * | 9/2013 | Kishigami | G01S 7/023 342/159 |
| 2014/0024917 | A1 * | 1/2014 | McMahon | A61B 5/4836 600/407 |
| 2015/0270923 | A1 * | 9/2015 | Dowla | H04W 4/90 455/1 |

FOREIGN PATENT DOCUMENTS

| | | |
|---|---|---|
| JP | 2009098098 A | 5/2009 |
| JP | 2002058659 A | 2/2014 |
| WO | 2014015238 A1 | 1/2014 |
| WO | 2015006364 A2 | 1/2015 |
| WO | 2016019292 A1 | 2/2016 |

OTHER PUBLICATIONS

Yiran Li, et al. "Wireless Radar Devices for Smart Human-Computer Interaction", XP032648806, pp. 65-68.
International Search Report for Application No. PCT/EP2016/058791, dated Aug. 4, 2016.
Adib, Fadel et al., Multi-Person Motion Tracking via RF Body Reflections, Computer Science and Artificial Intelligence Laboratory Technical Report, MIT-CSAIL-TR-2014-008, Apr. 26, 2014.
Zhou, Qin et al., Detection of Multiple Heartbeats Using Doppler Radar, pp. 1160-1163, ICASSP 2006.
Boric-Lubecke, Olga et al., Doppler Radar Sensing of Multiple Subjects in Singles and Multiple Antenna Systems, 7th International Conference on Telecommunications in Modem Satellite, Cable and Broadcasting Services Publication Year: 2005.
Japanese Office Action for Application No. JP2017-553397 dated Mar. 5, 2019.

* cited by examiner

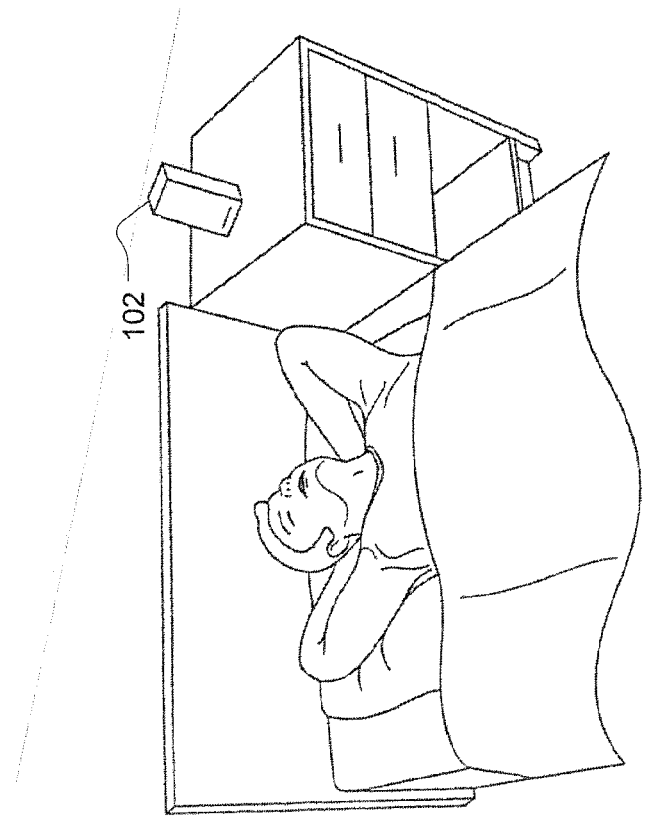
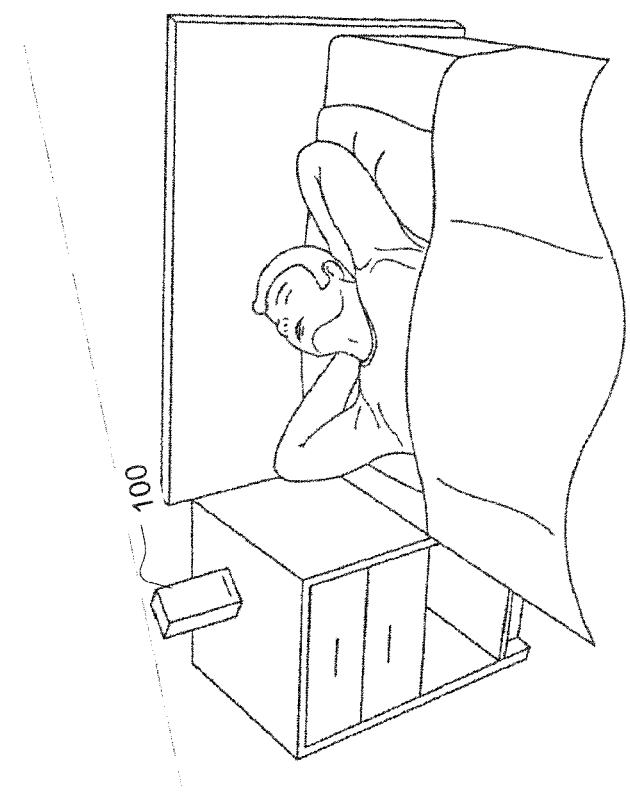
Fig. 1

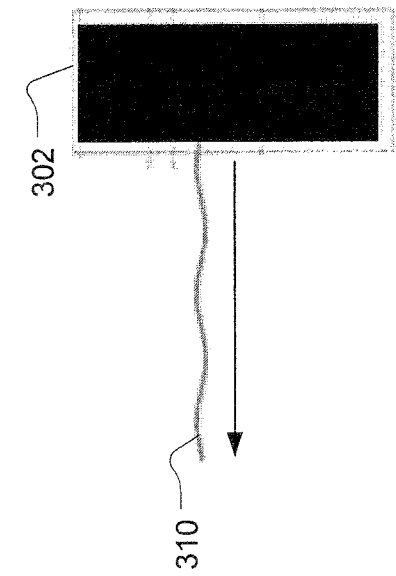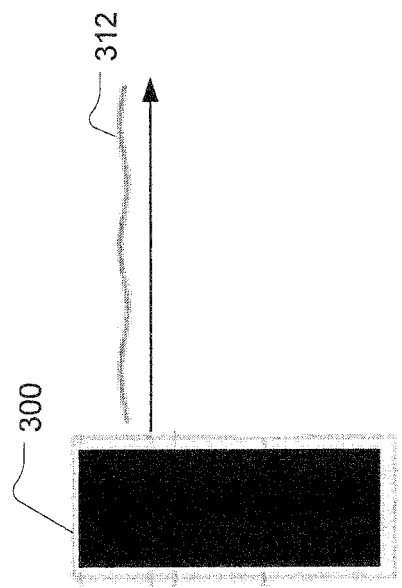
Fig. 2

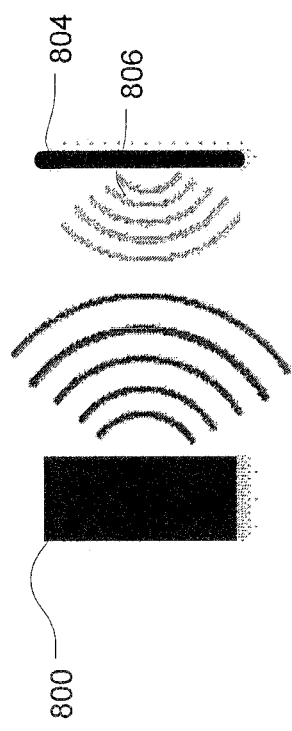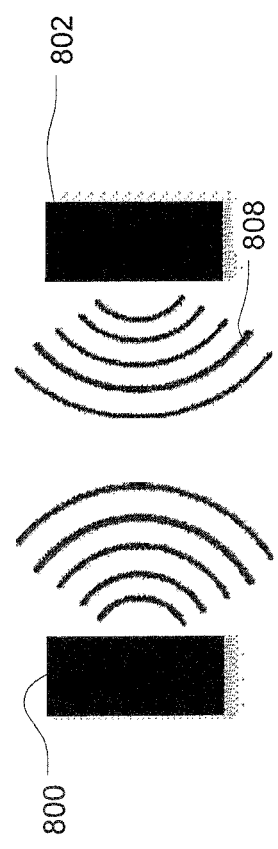

PRI signal, 0.5uS pulse width

MULTI SENSOR RADIO FREQUENCY DETECTION

CROSS-REFERENCE TO RELATED APPLICATIONS

The present application is a national phase entry under 35 U.S.C. § 371 of International Application No. PCT/EP2016/058791 filed Apr. 20, 2016, published in English, which claims priority from U.S. Provisional Patent Application No. 62/207,670, filed Aug. 20, 2015 and U.S. Provisional Patent Application No. 62/149,916, filed Apr. 20, 2015, all of which are incorporated herein by reference.

FIELD OF THE TECHNOLOGY

The present technology relates to circuits and sensors for detection of characteristics of moving objects and living subjects. More particularly, it relates to such sensors for generating radio frequency emissions, such as range gated pulses, motion sensing, with particular emphasis on improving sensor operation when in close proximity with similar sensors.

BACKGROUND OF THE TECHNOLOGY

Continuous wave (CW) Doppler radar motion sensors emit a continuous wave radio frequency (RF) carrier and mix the transmitted RF with the return echoes to produce a difference frequency equal to the Doppler shift produced by a moving target. These sensors do not have a definite range limit (i.e., they can receive signals for both near and far objects, with the received signal being a function of radar cross section). This can lead to false triggers i.e., motion artefact interference. They may also have an undesirably high sensitivity at close range that leads to false triggering.

A pulse Doppler motion sensor is described in U.S. Pat. No. 4,197,537 to Follen et al. A short pulse is transmitted and its echo is self-mixed with the transmitted pulse. The pulse width defines the range-gated region. When the transmit pulse ends, mixing ends and target returns arriving after the end of the transmit pulse are not mixed and are thereby gated out.

A Differential pulse Doppler motion sensor disclosed in U.S. Pat. No. 5,966,090, "Differential Pulse Radar Motion Sensor," to McEwan, alternately transmits two pulse widths. It then subtracts the Doppler responses from each width to produce a range gated Doppler sensing region having a fairly constant response versus range.

Impulse radar, such as that described in U.S. Pat. No. 5,361,070, "Ultra-Wideband Radar Motion Sensor," to McEwan produces a very narrow sensing region that is related to the transmitted impulse width. A two-pulse Doppler radar motion sensor, as described in U.S. Pat. No. 5,682,164, "Pulse Homodyne Field Disturbance Sensor," to McEwan, transmits a first pulse and after a delay generates a second pulse that mixes with echoes from the first pulse. Thus a range gated sensing band is formed with defined minimum and maximum ranges. UWB radar motion sensors have the disadvantage of not having global RF regulatory acceptance as an intentional radiator. They also have difficulty sensing objects at medium ranges and in some embodiments can be prone to RF interference.

A modulated pulse Doppler sensor is described in U.S. Pat. No. 6,426,716 to McEwan. The range gated microwave motion sensor includes adjustable minimum and maximum detection ranges. The apparatus includes an RF oscillator with associated pulse generating and delay elements to produce the transmit and mixer pulses, a single transmit (TX)/receive (RX) antenna or a pair of separate TX and RX antennas, and an RF receiver, including a detector/mixer with associated filtering, amplifying and demodulating elements to produce a range gated Doppler signal from the mixer and echo pulses.

In U.S. Pat. No. 7,952,515, McEwan discloses a particular holographic radar. It adds a range gate to holographic radar to limit response to a specific downrange region. McEwan states that cleaner, more clutter-free radar holograms of an imaged surface can be obtained, particularly when penetrating materials to image interior image planes, or slices. The range-gating enables stacked hologram technology, where multiple imaged surfaces can be stacked in the downrange direction.

In U.S. Patent Application Publ. no. 2010/0214158, McEwan discloses an RF magnitude sampler for holographic radar. McEwan describes that the RF magnitude sampler can finely resolve interferometric patterns produced by narrowband holographic pulse radar.

In U.S. Patent Application Publication No. 2014/0024917, McMahon et al, describe a sensor for physiology sensing that may be configured to generate oscillation signals for emitting radio frequency pulses for range gated sensing. The sensor may include a radio frequency transmitter configured to emit the pulses and a receiver configured to receive reflected ones of the emitted radio frequency pulses. The received pulses may be processed to detect physiology characteristics such as motion, sleep, respiration and/or heartbeat.

There may be a need to improve sensors and/or their signal processing for radio frequency sensing such as in the case of physiological characteristic detection when multiple sensors are in a common location. Sensor proximity can have undesirable interference. For example, this can deteriorate the signal to noise ratio.

SUMMARY OF THE TECHNOLOGY

One aspect of some embodiments of the present technology relates to a sensor for detecting physiology characteristics with radio frequency signals.

Another aspect of some embodiments of the technology relates to such a sensor with a circuit configured to generate pulsed radio frequency (RF) signal that is transmitted towards a subject, e.g., a human. A receiver detects signal reflected from the subject, which signal is amplified and mixed with a portion of the original signal. The output of this mixer may then be filtered. The resulting signal may contain information about the movement, respiration and cardiac activity of the person, for example, and may be referred to as the raw motion sensor signal. The phase difference between the transmitted signal and the reflected signal may be measured, either at the receiver or by an independent processor, in order to estimate any one of the general body movement, respiration and cardiac activity of the person.

In some versions, the RF motion sensors may be configured to reduce interference from other RF motions sensors.

In some versions, the sensors may be configured to synchronize amongst a group of local sensors to avoid overlap in RF pulses in time.

In some versions, the sensors may be configured to synchronize amongst a group of local sensors to avoid overlap in RF pulses in frequency.

In some versions, the signal pulsing from each sensor may be adapted to reduce probability of interference by various means described herein, such as for example, by pulse width reduction, timing dithering and/or frequency dithering.

In some versions, multiple (e.g., two) sensors may be configured, such as with a common housing structure, to face in different or suitable directions to avoid interference (e.g., placed midway along the bed at the headboard or at feet).

In some versions, multiple sensors may allow for optimum placement to mitigate the noise. These versions could depend on the sensor antenna polarisation or antenna beam pattern to provide the necessary RF interference attenuation.

Some versions of the present technology may include a radio frequency motion sensor configured for operation in a multi-sensor configuration. The radio frequency motion sensor may include a radio frequency transmitter. The transmitter may be configured to emit sensing signals such as pulsed radio frequency signals. The radio frequency motion sensor may include a receiver configured to receive reflected ones of the emitted radio frequency signals to detect motion of a reflecting surface. The transmitter may be configured for synchronized transmission of the pulsed radio frequency signals with another radio frequency motion sensor in the vicinity of the radio frequency motion sensor to mitigate interference between emitted pulses from the radio frequency motion sensors.

In some versions, the transmitter may be synchronized in time to interleave emitted pulsed radio frequency signals with emitted pulsed radio frequency signals of another radio frequency motion sensor. Synchronization between the radio frequency motion sensors may involve transmission of a clock signal. The synchronization between the radio frequency motion sensors may involve transmission of a dither synchronous signal. Optionally, the radio frequency motion sensor detects or may detect timing from an emitted pulsed radio frequency signal. In some versions, the radio frequency motion sensor may detect a synchronization signal independent of the emitted pulsed radio frequency signal. The radio frequency motion sensor may include an infra-red signal transmitter adapted for timing of the emitted pulsed radio frequency signals. The radio frequency motion sensor may include an interface for wired connection with another radio frequency motion sensor. The wired connection may be configured for timing of the emitted pulsed radio frequency signals. The transmitter may be synchronized with a transmitter of another sensor with respect to frequency to reduce interference.

Optionally, the transmitter may include a variable oscillator configured for frequency adjustment in response to detected interference noise. The transmitter may be further configured for frequency dithering. The transmitter may be further configured for time dithering. The transmitter may be configured to dither the frequency of the pulsed radio frequency signals.

Some versions of the present technology may include a radio frequency motion sensor. The radio frequency motion sensor may include a radio frequency transmitter configured to emit radio frequency sensing signals such as pulsed radio frequency signals; and a receiver configured to receive reflected ones of the emitted radio frequency signals to detect motion of a reflecting surface. The transmitter may be configured with a dither timing different from a dither timing of another radio frequency motion sensor in the vicinity of the radio frequency motion sensor to mitigate interference between emitted pulses from the radio frequency motion sensors. The dither timing of the transmitter may be pseudo random. The transmitter may be configured with frequency dithering.

Some versions of the present technology may include a radio frequency motion sensing apparatus. The apparatus may include two or more radio frequency sensors. Each sensor may include a radio frequency transmitter configured to emit sensing signals such as pulsed radio frequency signals and a receiver configured to receive reflected ones of the emitted radio frequency signals to detect motion. The apparatus may include comprises a housing to maintain the sensors in a configuration to emit the radio frequency signals in different directions to mitigate interference between emitted pulses from the radio frequency motion sensors. The sensors may be so positioned to direct the emitted pulses at a relative angle of about 90 degrees to 270 degrees. The sensors may be positioned to direct the emitted pulses at a relative angle of about 180 degrees or greater.

Some versions of the present technology may include a system for transmitting radio frequencies such as for sensing. The system may include a master radio frequency motion sensor and a slave radio frequency motion sensor. The master radio frequency motion sensor may be configured to transmit a first radio frequency (RF) signal. The slave radio frequency motion sensor may be configured to transmit a second RF signal. The system may be arranged or configured to minimise the interference between the RF signals of both sensors.

In some versions, the slave radio frequency motion sensor may be configured to transmit a second RF signal that creates minimal interference with the first RF frequency signal. The master radio frequency motion sensor and slave radio frequency motion sensor may be adapted within a single or common housing. The master radio frequency motion sensor and slave radio frequency motion sensor may be positioned within the single or common housing at an angle of 90 degrees, approximately. The RF transmitter may be configured to transmit at least one synchronization RE pulse signal. The slave radio frequency motion sensor may be further configured to receive the synchronization RF pulse signal. The slave radio frequency sensor may be further configured to detect the received synchronization RF pulse signal at an intermediate frequency. The master radio frequency sensor may be further configured to transmit the at least one RF pulse signal on a separate industrial, scientific and/or medical transmission band (ISM). The master radio frequency sensor may further include an infra-red (IR) transmitter such as one configured to transmit an IR synchronization signal. The slave radio frequency sensor may include an infra-red (IR) receiver such as one configured to receive the transmitted IR synchronization signal.

Optionally, the master radio frequency sensor and the slave radio frequency sensor may further include a master-slave oscillator circuit. The master-slave oscillator circuit may further include a multi-wire cable interconnection such as one configured to transmit timing and dithering synchronization information from the master radio frequency sensor to the slave radio frequency sensor. At least one of the master radio frequency motion sensor and the slave radio frequency motion sensor may include at least one resonator oscillator circuit. At least one resonator oscillator circuit may include a quartz crystal.

In some versions, the slave radio frequency motion sensor may include the at least one resonator oscillator circuit as well as a voltage controlled RF oscillator. The voltage controlled RF oscillator may be configured to synchronize its RF signal frequency to the master radio frequency motion sensor. The voltage controlled RF oscillator may be configured to synchronize the RF frequency to the master radio frequency sensor by detecting a high voltage which result in a high level of interfering noise, detecting a low voltage which result in a high level of interfering noise and moving the voltage controlled RF oscillator to a central control voltage position between the high and low voltage. Optionally, at least one of the first RF signal and second RF signal may have an RF pulse width of about 0.5 μs.

The master radio frequency sensor may be configured to provide a first dithering time to the first RF signal. The slave radio frequency sensor may be configured to provide a different dithering time to the second RF signal. The master radio frequency sensor may include a first binary ripple counter and exclusive OR gate. Similarly, the slave radio frequency sensor includes a second binary ripple counter and exclusive OR gate. The first and second binary ripple counter and exclusive OR gates may be configured to create a pseudo random dithering time. The master radio frequency sensor may include a first dielectric resonant oscillator that may be modulated by a first voltage. The slave radio frequency sensor may include a second dielectric resonant oscillator that may be modulated by a second voltage. Optionally, the first and second RF signals may be at different frequencies.

Some versions of the present technology may include a system for transmitting radio frequencies, such for sensing. The system may include a first radio frequency motion sensor and a second radio frequency motion sensor. The first radio frequency motion sensor may be configured to transmit a first radio frequency (RF) signal. The second radio frequency motion sensor may be configured to transmit a second RF signal. The system may be adapted to minimise the interference between the RF signals of both sensors.

In some versions, the first frequency motion sensor may be configured to receive an indication of the frequency transmitted from the second radio frequency motion sensor, and the second radio frequency motion sensor may be configured to receive an indication of the frequency transmitted from the first radio frequency motion sensor. The first frequency motion sensor may be configured to adjust the frequency of the first radio frequency signal in response to the received indication of the frequency transmitted from the second radio frequency motion sensor. Each of the first frequency motion sensor and the second frequency motion sensor may be configured to access a lookup table which includes selectable frequencies at which the sensors can operate. The first frequency motion sensor may be configured to select a frequency from a first lookup table, and the second frequency motion sensor may be configured to select a frequency from a second lookup table. The first lookup table may include odd frequencies and the second lookup table may include even frequencies. The first frequency motion sensor and the second radio frequency motion sensor may be configured to adjust their respective frequencies using a network time protocol (NTP).

The first frequency motion sensor and the second radio frequency motion sensor may be configured to adjust their respective transmission frequencies in response to detecting interference. The first frequency motion sensor and the second radio frequency motion sensor may be configured to adjust their respective transmission frequencies based on predetermined temperature coefficients. The first frequency motion sensor and the second radio frequency motion sensor may be configured to check or adjust the frequency at which they transmit RF signals in response to input of geographical location. At least one of the first frequency motion sensor and the second radio frequency motion sensor may be configured to operate in a low power mode upon detection of an absence of motion. The first frequency motion sensor and the second radio frequency motion sensor may be configured to send a continuous clock signal over a wired or wireless link.

In some versions, at least one of the first frequency motion sensor and the second radio frequency motion sensor may be configured to: send periodic centre frequency values read from each respective sensor over a network; and/or adjust the frequency at which each sensor transmits to minimise interference between the first and second sensors. At least one of the first frequency motion sensor and the second radio frequency motion sensor may be configured to: dynamically detect its respective current centre frequency; and/or periodically adjust such frequency in order that it matches an agreed lookup table centre frequency so the interference between the two sensors is minimized, while remaining within a defined spectral mask. Optionally, the first frequency motion sensor and the second radio frequency motion sensor may be configured so that: a frequency range may be dynamically scanned to detect minimum and maximum interference; and/or a centre frequency of at least one of the sensors may be adjusted to a frequency associated with the minimum. The sensors may communicate via a frequency of maximum interference. At least one of the first frequency motion sensor and the second radio frequency motion sensor may be configured to: detect a temperature change; and/or initiate polling between the sensors, based on the detected temperature change, for adjusting a centre frequency of at least one of the sensors.

In some versions, system may be arranged to minimise interference between the RF signals of both sensors by frequency dithering of one or more oscillators of the sensors generating the RF signals. For example, a voltage level to at least one of the one or more oscillators may be ramped to produce the frequency dithering. The system may be arranged to minimise interference between the RF signals of both sensors by timing dithering of pulses of the RF signals of both of the sensors. For example, a voltage level to a diode coupled with at least one of the one or more oscillators may be ramped to implement the timing dithering of at least one of the sensors. In some cases, the at least one of the one or more oscillators may be a dielectric resonant oscillator.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIG. 1 is an illustration of an example detection system suitable for implementation with a radio frequency physiology sensor of the present technology;

FIG. 2 is a conceptual diagram illustrating a an operation of some embodiments of the technology;

FIGS. 8A and 8B are diagrams showing examples of signal paths travelled by RF signal as found in some embodiments of the present technology;

DETAILED DESCRIPTION

1. Overview

As illustrated in FIG. 1, some embodiments of the present technology may implement sensing or detection apparatus 100 and 102, useful for detecting physiological characteristics of multiple users or patients. The sensors may be standalone sensors or may be coupled with other apparatus, such as a respiratory treatment apparatus, so as to provide an automated treatment response based on an analysis of the physiological characteristics detected by the sensors of the apparatus. For example, a respiratory treatment apparatus with a controller and a flow generator may be configured with such a sensor or to communicate with such a sensor and may be configured to adjust a pressure treatment generated at a patient interface (e.g., mask) in response to physiological characteristics detected by the sensor. Or such a sensor might be used to detect physiological characteristics of a patient when the flow generator is not in use by the patient to inform them of the advantage of using the flow generator. An example respiratory treatment apparatus is described in International Patent Application No. PCT/US2015/043204, filed on Jul. 31, 2015, the entire disclosure of which is incorporated herein by reference.

A typical sensor of such an apparatus may employ a transmitter to emit radio frequency (RF) waves, such as radio frequency pulses for range gated sensing. A receiver, which may optionally be included in a combined device with the transmitter, may be configured to receive and process waves reflected from the patient's body. Signal processing may be employed, such as with a processor of the apparatus that activates the sensor, to derive physiological characteristics based on the received reflected signals. An example of the operation of such a sensor can be found in U.S. Patent Application Publ. No. 2009/0203972, the entire disclosure of which is incorporated herein by reference.

Figure 3:
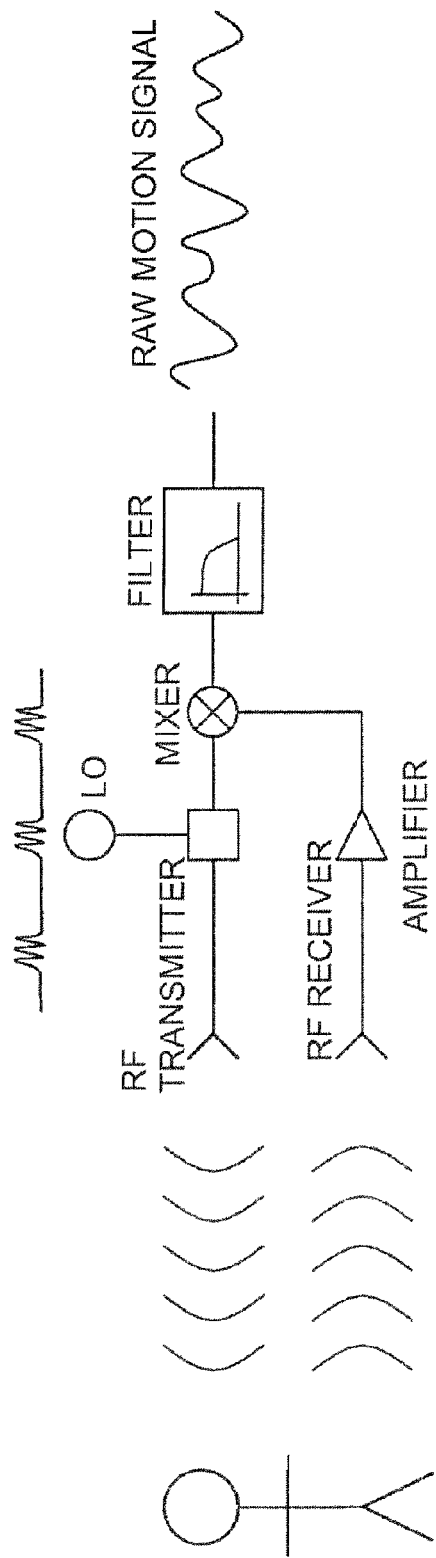
FIG. 3 is a diagram illustrating a conceptual structure and process flow for obtaining sensor signals suitable for some embodiments of the technology.

A principal diagram of a sensor, or of a component of the sensor, is shown in FIG. 3. As illustrated in FIG. 3, the transmitter transmits a radio-frequency signal towards a subject, e.g., a human. Generally, the source of the RF signal is a local oscillator (LO). The reflected signal is then received by the RF receiver, amplified and mixed with a portion of the original signal, and the output of this mixer may then be filtered. The resulting signal may contain information about the movement, respiration and cardiac activity of the person, for example, and is referred to as the raw motion sensor signal. The phase difference between the transmitted signal and the reflected signal may be measured in order to estimate any one of the movement, respiration and cardiac activity of the person.

The raw motion sensor signal can be processed to obtain signal components reflecting bodily movement, respiration and cardiac activity. Bodily movement can be identified by using zero-crossing or energy envelope detection algorithms (or more complex algorithms), and used to form a "motion on" or "motion off" indicator. For example, such movement detection algorithms may be implemented in accordance with the methodologies disclosed in any of U.S. Patent Application Publ. No. 2009/0203972, mentioned previously, International Patent Application No., PCT/US14/045814; U.S. Provisional Patent Application No. 62/149,839, filed Apr. 20, 2015, and U.S. Provisional Patent Application No. 62/207,687, filed Aug. 20, 2015, the entire disclosures of which are each incorporated herein by reference. The respiratory activity is typically in the range 0.1 to 0.8 Hz, and can be derived by filtering the original signal with a bandpass filter with a passband in that region. The cardiac activity is reflected in signals at higher frequencies, and this activity can be accessed by filtering with a bandpass filter with a pass band of a range from 0.8 to 10 Hz (e.g., 70 heart beats per minute is within this range at around 1.17 Hz).

Such a respiration and movement sensor may be a range gated RF motion detector. The sensor may be configured to accept a DC power supply or battery input and provide, for example, four analog motion channel outputs with both in-phase and quadrature components of the respiration and movement signals of a person within the detection range. In the case of a pulsed RF motion sensor, range gating can help to limit movement detection to only a preferred zone or range. Thus, detections made with the sensor may be within a defined distance from the sensor.

Figure 4:
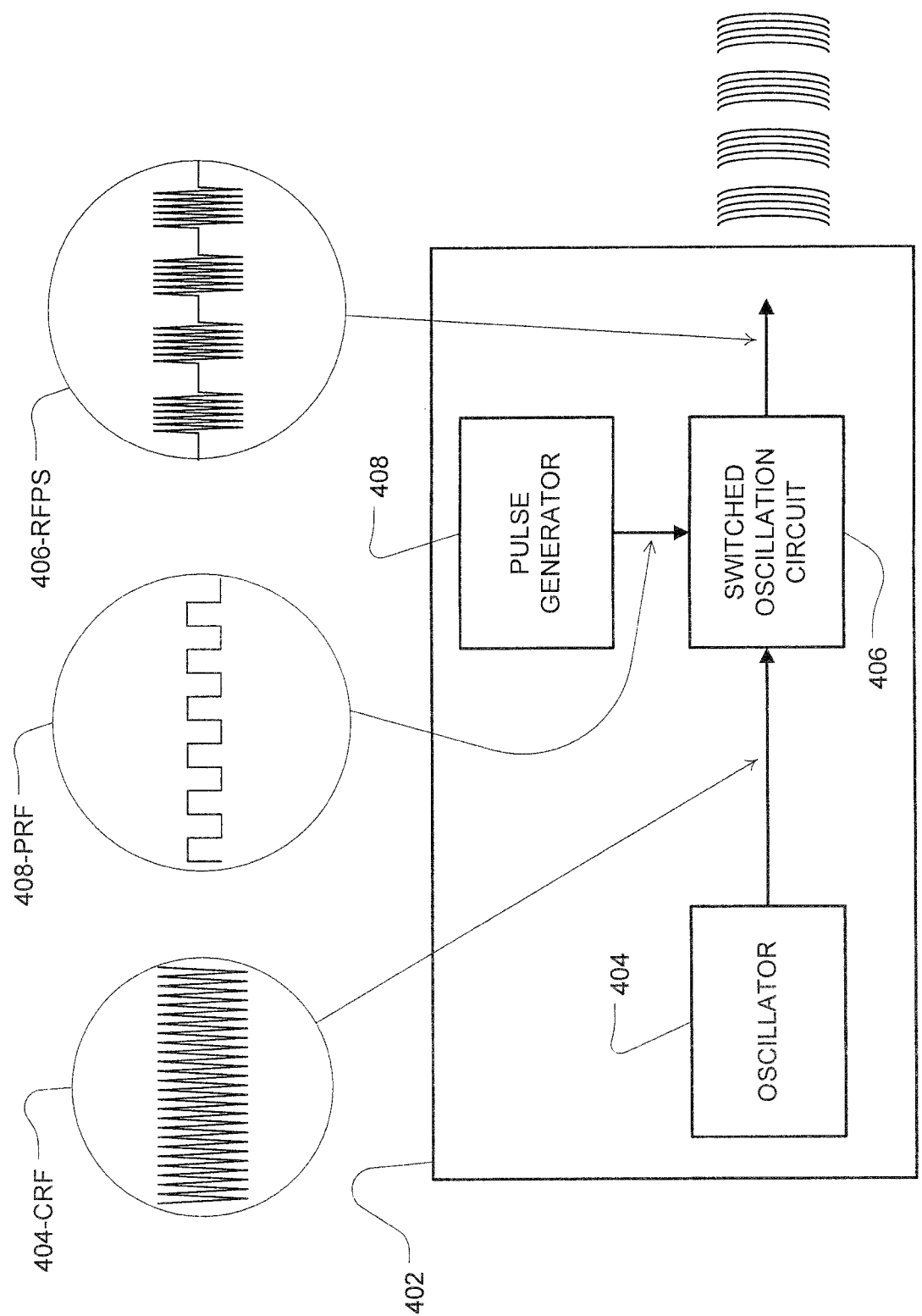
FIG. 4 shows example components involved in a generation of range gated radio frequency signals with switched oscillation in some embodiments of a sensor circuit for the present technology.

As illustrated in FIG. 4, a typical sensor 402 of the present technology may employ one or more oscillators, such as an oscillator 404, such as a dielectric resonant oscillator (DRO). The DRO may be a high Q DRO that is a narrow-band oscillator (e.g., a DRO operating at 10.525 GHz), such as an oscillator incorporating a puck of dielectric material. The DRO typically generates a stable RF frequency characteristic and is relatively immune to variation in temperature, humidity and component parasitics. In some cases, the sensor may be a sensor described in U.S. Patent Application Publication No. 2014/0024917, the entire disclosure of which is incorporated herein by reference.

Figure 5A:
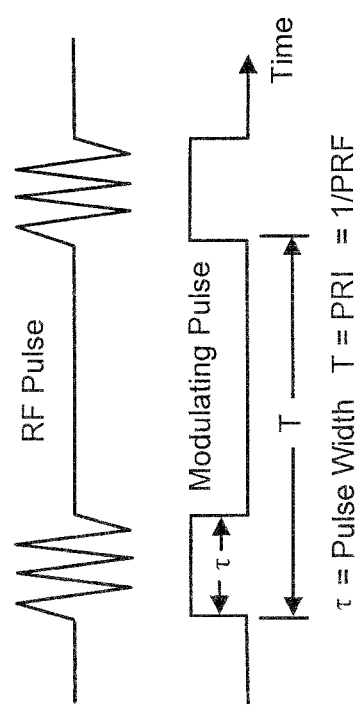
FIGS. 5A and 5B are diagrams illustrating the creation and detection of an RF pulse suitable for some embodiments of the technology.

As illustrated in FIG. 5A, the pulsed radio frequency signal has two main modulation parameters. These are the pulsed repetition interval (PRI), with time duration represented by T, and the pulse width (PW), with time duration represented by τ. The term pulsed repetition frequency (PRF) is the inverse of the PRI. For example, a sensor may transmit a 10.525 GHz RF signal which was pulse modulated at a frequency of approximately 250 KHz to create an RF pulse signal with a pulse repetition interval designated T of 4 µs and a pulse width timing designated τ of 2 µs. Accordingly, the RF signals in the example would be 0.5 µs long and produced every 4 µs (i.e., a 12.5% duty cycle).

The sensor may be a homodyning transceiver capable of both transmitting and receiving RF signals. As such, the transceiver may measure the magnitude and phase of the received signal with respect to the transmitted signal. The phase and/or magnitude of the received signal changes with respect to the transmitted signal when the target moves or upon the distance the received signal travelled. As a result, the demodulated magnitude detector receiver output signal is a measure of the movement of a target and/or the distance the signal travelled. While such a magnitude detector may be optionally implemented, in some cases, other circuit elements or detectors may be implemented in place of or to serve the function of the magnitude detector(s). For example, any detector circuit configured to detect signal modulation, such as a peak detector, envelope detector, or harmonic mixer circuit may be employed.

Figure 5B:
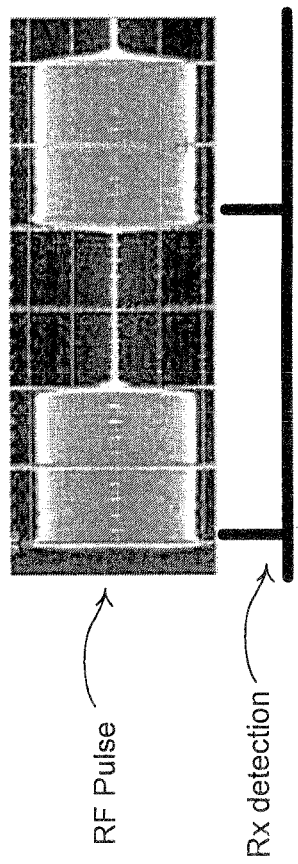

Both transmitted RF signals and received RF signals may be presented to the input of a homodyning receiver switched magnitude detector (e.g., an RF magnitude detector). For example, as shown in FIG. 5B, a received signal may be detected during a receive time interval period when the sensor is transmitting an RF pulse. In this regard, the magnitude detector may detect RF pulses every time an RF pulse is transmitted. In some embodiments, the magnitude detector may detect signals during a 5 ns period during the first 12 ns of a RF pulse transmission (i.e., the 5 ns could be anywhere within the first 12 ns, e.g. starting at the $7^{th}$ ns, $1^{st}$ ns etc.).

When only a single source of RF pulses is present, the transmitted and received RF signals may be represented with the following mathematical formulas:

Transmitted RF signal: $A \sin(\omega 1 t + \theta 1)$; and

Received RF signal: $B \sin(\omega 1 t + \theta 2)$

Where A and B are amplitudes, ω1 is the angular frequency, t is the time, and θ1 and θ2 are respective phases. (Time travelled is implicit in the phase difference between θ1 [e.g., reference phase at oscillator] and θ2 [after bouncing off the subject]).

As the two signals are from the same source, they also have the same frequency. Accordingly, when they are superimposed the resulting RF signal has an amplitude that varies with phase and amplitude of the reflected signal. The transmitted RF signal and received RF signal may be combined by using the following formulas where a and b are amplitudes, x is a time multiplied angular frequency (2πft), and β and α are phases.

Figure 6:
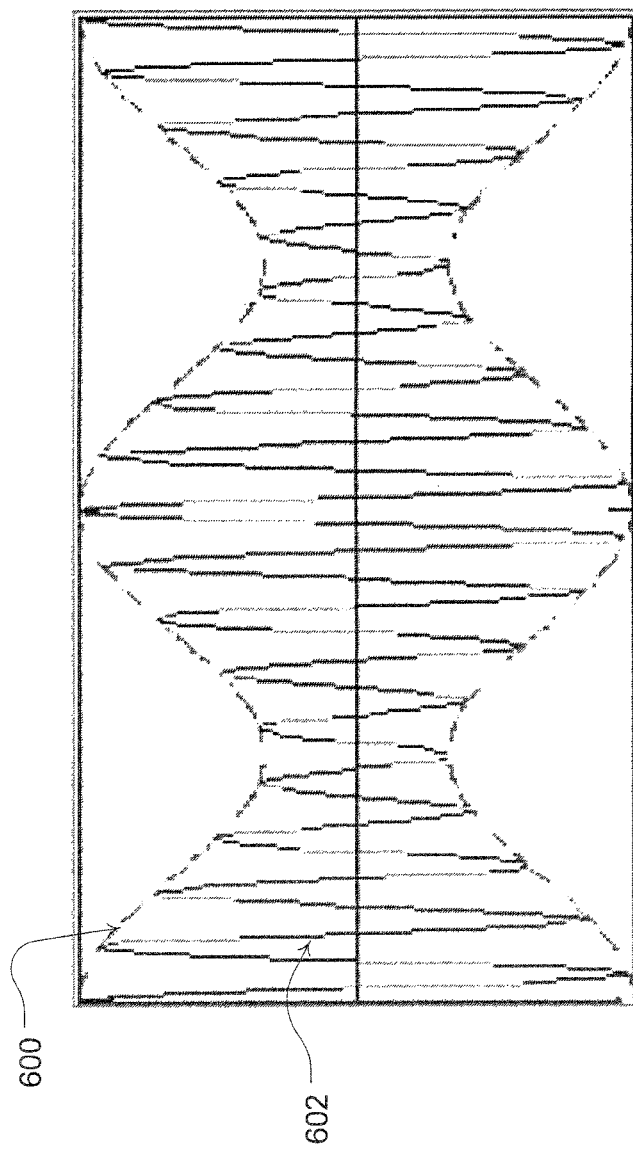
FIG. 6 is an illustration of the resultant receiver RF signal suitable for some embodiments of the technology.

As shown in FIG. 6, a resulting signal 602 may be the result of a transmitted RF signal being modulated by a received RF signal. The resulting signal 602 may have a periodic sinusoidal amplitude envelope 600 and phase that varies only respective of distance and movement of a target. Accordingly, the superimposed signal varies with the distance to a target or target movement.

Time Dithering

Figure 10A:
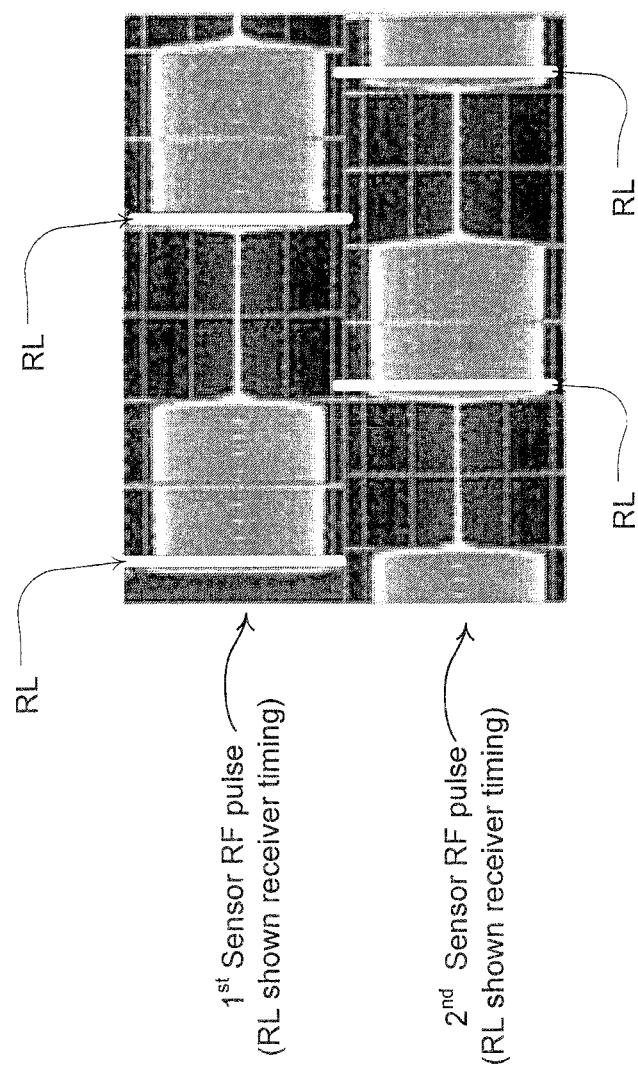
FIG. 10A is a signal representation of synchronous timing of the pulse generation.
Figure 10B:
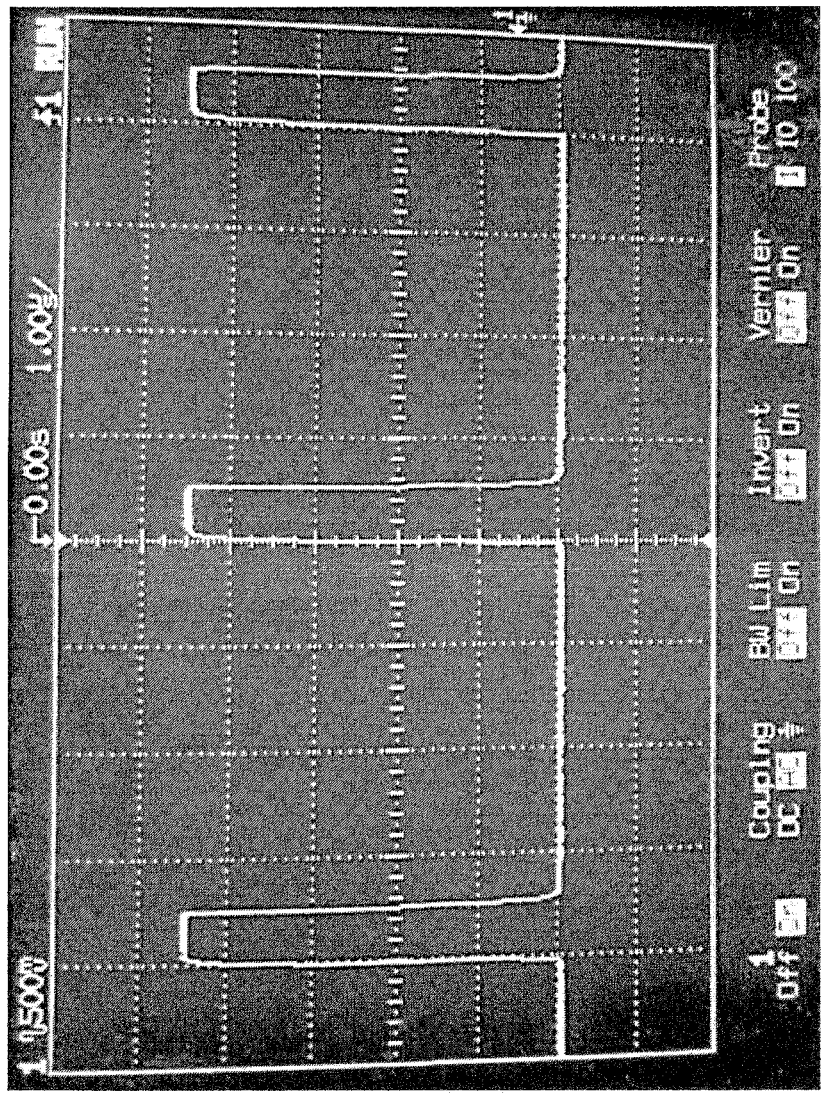
FIG. 10B is a signal representation of "dithering" of the pulse generation.

When operating two or more sensors, oscillator timing differences and/or dithering may promote noise interference reduction. For example, in some sensors, the timing of the pulse generation may be dithered with respect to the timing associated with the underlying pulse repetition frequency by inclusion of a dithering circuit (not shown) such as one coupled with or included with a pulse generator 408. FIG. 10b shows a signal representation of "dithering" of the pulse generation (in which the onset time of the pulse varies with respect to the overall pulse generation timing). With such dithering, the overall pulse repetition frequency can be varied, so that the pulse onset time is linearly delayed or advanced with respect to the nominal overall pulse center (i.e., a second pulse train is at a slower pulse repetition frequency than a first pulse train). This has the net effect of changing the position of the pulse onset time, compared to its nominal onset time if the PRF remained fixed. This may be achieved with a synchronous ramp dithering circuit. An example synchronous ramp dithering circuit may be implemented with a voltage controlled delay element based on an underlying RC (resistor-capacitor) time constant. The ramp control voltage results in a varying varactor capacitance which in turn results in a varying resonator frequency. In this way the frequency of the pulse generation circuit oscillator and associated PRF is varied on the order of about 1% in a synchronous and linear manner every 1 ms approximately. In some examples, the linear ramp function may be at 1 kHz, which produces an associated dither on the PRI and PW timing. Dithering may be utilised to remove synchronous RF demodulation noise artefacts. Ramp dithering may be utilised because it is less complex to implement, however it can produce tone artefacts if not synchronous with the RF modulation and demodulation timing. Synchronous ramp dithering prevents these unwanted tones from being generated. However, the use of a timing dithering circuit complicates the unit to unit PRI timing difference and hence complicates pulse timing synchronization.

Figure 17:
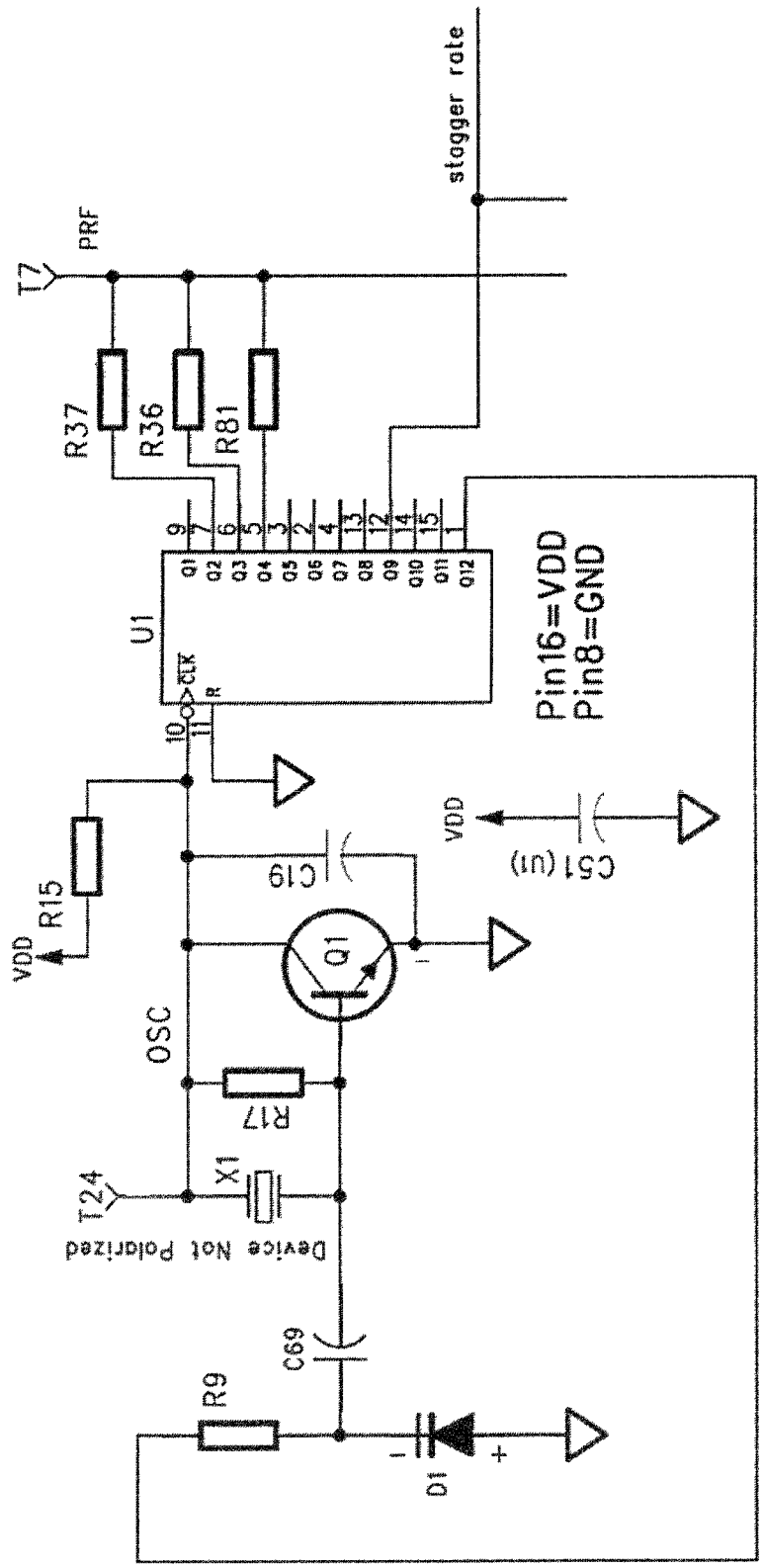
FIG. 17 shows a sample schematic of how RF modulation and demodulation timing is established by a 4 MHz ceramic resonator oscillator and associated binary ripple counter.

In some sensors, RF modulation and demodulation timing is established by a 4 MHz ceramic resonator oscillator and associated binary ripple counter (see example of FIG. 17). To achieve low demodulation noise, the oscillator timing may be subsequently "synchronously dithered" with a linear ramp function (e.g., at 1 kHz) which produces an associated dither on the PRI and PW timing. This use of a timing dithering circuit complicates the unit to unit PRI timing difference. This timing difference is further compounded by the use of a ceramic resonator which has a lower frequency tolerance and higher drift compared to that of a quartz crystal. In summary, although synchronous dithering can mitigate RF interference signal noise it creates issues for a second method of RF interference signal noise reduction, namely pulse timing synchronization, due to dithering and/or the timing difference. For example, as shown in FIG. 10A the read signals of the $1^{st}$ sensor may overlap with the pulse of the $2^{nd}$ sensor and vice-versa.

Figure 11A:
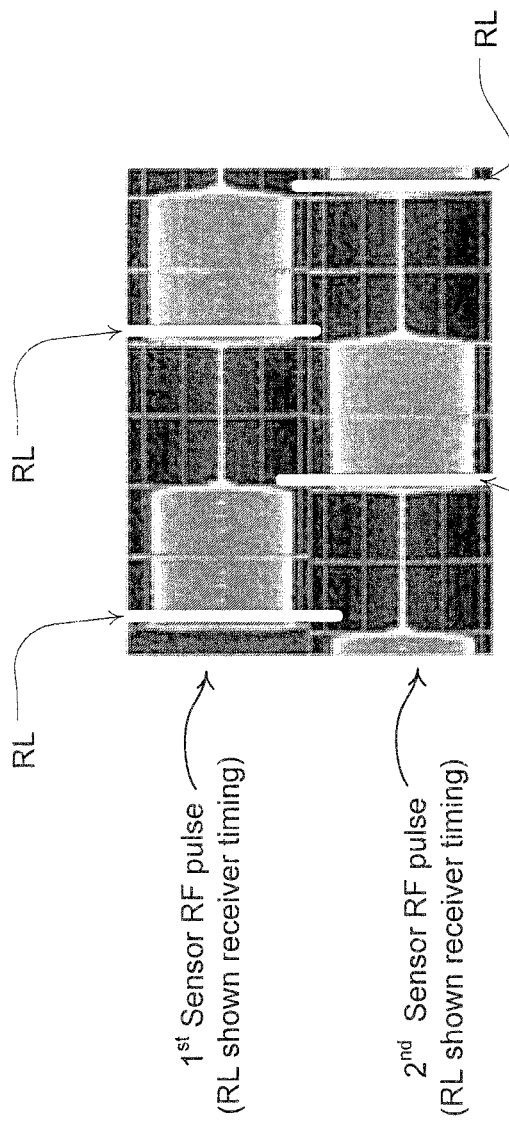
FIG. 11A is a signal representation of asynchronous timing of the pulse generation and reading.
Figure 11B:
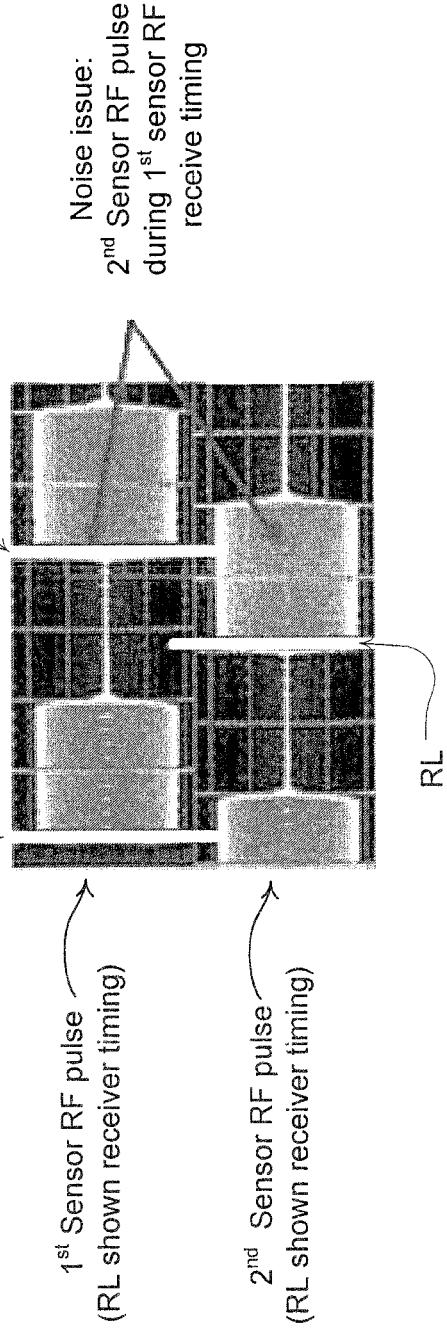
FIG. 11B is a signal representation of overlapping signals as described in the present technology.

For two sensors to coexist without producing RF interference the first sensor should transmit its RF pulse in the quiet period of the second sensor and vice versa. For example, as shown in FIG. 11A, the read signals (white lines/indicated as "RL" on the Figure) of the first sensor occur only during the time periods during which the second sensor is not transmitting a RF signal. Similarly, the second sensor only reads signals when the first sensor is not transmitting. However, in practice the asynchronous nature of the sensor operations (dithering, frequency difference and frequency drift) results in periodic overlap of the RF pulse of the first sensor with the receive timing of the second sensor, as shown in FIG. 11B. In this regard, due to the nature of the sensors, the read signals of the first sensor may occur during the transmission of an RF pulse by the second sensor and vice-versa.

2. Sources of Noise

Sensors, such as the sensors of illustrated detection apparatus 100 and 102 which are positioned within close proximity of each other, may suffer from radio frequency (RF) coexistence issues. As illustrated in FIG. 2, two sensors 300 and 302 may be placed so that their respective RF pulses are projected in the direction of the opposing sensor. In this regard, sensor 300 may transmit RF pulse 312 in the direction of sensor 302, and sensor 302 may transmit RF pulse 310 in the direction of sensor 300. As a result, the sensor 300 may receive the reflection of its RF pulse 312, the direct RF pulse 310 of the opposing sensor 302, as well as the opposing sensor's double-reflection RF pulses (not shown). Accordingly, the RF pulses received by a sensor may include more than just the desirable RF pulse reflections created by the RF signal that the sensor originally transmitted, resulting in baseband interference when the received RF pulses are demodulated. (Generally, in some cases, a baseband signal may be a signal that has a very narrow frequency range, i.e. a spectral magnitude that is nonzero only for frequencies in the vicinity of the origin (termed f=0) and negligible)).

While only RF pulses of the sensors are shown in FIG. 2, RF waves from other apparatus may also be received by the sensors. Such RF waves may come from apparatus located both near and far from the sensors. Due to the nature of RF waves, they may possess the ability to travel through barriers such as walls and other obstacles and geographical topography. Accordingly, embodiments of the present technology may be directed to significantly diminishing the sensors' susceptibility to RF coexistence issues.

When received RF signals come from an apparatus or source other than the transmitting sensor, noise may be introduced into the received RF signals. The transmitted, received and resultant RF signals may be represented with the following mathematical formulas:

RF signal transmitted by the first source:

$A \sin(\omega_1 t + \theta_1)$; and

RF signal received at the second source:

$A \sin(\omega_2 t + \theta_2)$

Figure 7:
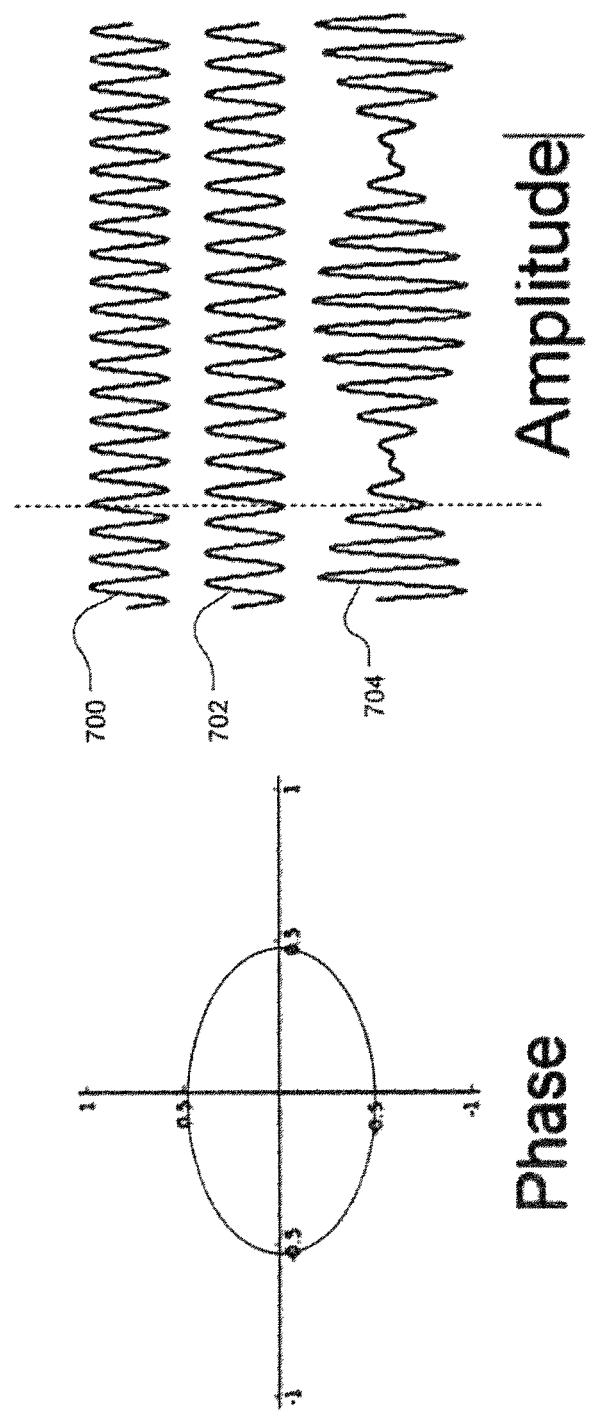
FIG. 7 is an illustration of the transmitted signal (700), received signal (702) and the resultant receiver RF signal (704); which includes baseband noise, as described in the present technology. The constant variations seen in the resultant receiver RF signal (704) may lead to baseband interference.

Resultant Combined RF Signal:

$$A\cos 2\pi f_1 t + A\cos 2\pi f_2 t = 2A\cos 2\pi \frac{f_1 - f_2}{2} t \cos 2\pi \frac{f_1 + f_2}{2} t$$

Where A and B are amplitudes, $\omega_1 t$ and $\omega_2 t$ are respective time dependent angular frequencies, and $\theta 1$ and $\theta 2$ are respective phases. Combining the transmitted signal from the first source and received RF signal from the second source may result in an RF signal with a periodic sinusoidal amplitude envelope and phase that constantly varies in time irrespective of any movement of a target. In the example of FIG. 7, transmitted signal 700 from a first source may be combined with a signal 702 received from a second source, producing resulting signal 704. As can be seen, the resulting signal 704 has a periodic sinusoidal amplitude envelope and phase that constantly varies in time irrespective of any movement of a target. (As the phase is constantly changed with time, this is represented as a circle in FIG. 7 [left hand side]). Such constant variations to the resulting signal may be introduced when the received signal 702 is combined with the transmitted signal 700 at a multiple of the intermediate frequency of the transmitted frequency. Such variations may lead to baseband interference.

The amount of interference generated by an RF signal transmitted from an apparatus or source other than the receiving sensor may be dependent on the received signal strength of the unwanted interfering RF signal. In this regard, the unwanted interfering RF signal's strength may be dependent upon the path the interfering RF signal travels before arriving at the receiving sensor. For example, as shown in FIG. 8A, an interfering signal 806 may be reflected off of an object 804 and received by the receiving sensor 800. Accordingly, the power of the interfering RF signal 806 is reduced when it arrives at the receiving sensor 800, compared to the case when the signal arrives directly at the receiving sensor 800. The formula for the power of the interfering signal after being reflected is given by:

$$P_r = \frac{P_t G_t A_r \delta F^4}{(4\pi)^2 R_r^4}$$

Wherein:

$P_r$=power of the interfering signal which has been reflected;

$P_t$=transmitter power;

$G_t$=gain of the transmitting antenna;

$A_r$=effective aperture (area) of the receiving antenna (most of the time noted as Gr);

$\delta$=radar cross section, or scattering coefficient, of the target;

$R_r$=distance from the transmitter to the target (for a reflected signal) and

F=pattern propagation factor (Normally close to 1)

In contrast, as shown in FIG. 8B, an interfering signal 808 may be generated by a second active source 802 and received directly by sensor 800, without incurring any reflections. As no reflection of the interfering signal 808 occurs, the power of the interfering signal 808 is only reduced based on distance travelled. Accordingly, the power of the interfering RF signal is reduced based on distance. The formula for the power of the interfering signal 808 which has not been reflected but directly arrives at the receiver is given by:

$$P_d = \frac{P_t G_t A_r \delta F^4}{(4\pi)^2 R_d^2}$$

Wherein:

$P_d$=power of the interfering signal which has not been reflected;

$P_t$=transmitter power;

$G_t$=gain of the transmitting antenna;

$A_r$=effective aperture (area) of the receiving antenna (most of the time noted as Gr);

$\delta$=radar cross section, or scattering coefficient, of the target;

$R_d$=distance from the transmitter to the receiver. (for a direct transmit to receive); and F=pattern propagation factor (Normally close to 1)

As a result, when two sensors are placed in a room, the interfering signal level from the second unit can be higher than the signal transmitted by the first sensor and reflected back to the first sensor because of the shorter effective path length and the absence of attenuation due to scattering.

When an interfering RF signal is received at a sensor, the interfering RF signal will cause baseband noise under certain conditions: (1) the interfering RF frequency is in-band (i.e. close to 10.525 GHz, 10.587 GHz, 9.3 GHz, 61 GHz, 24 GHz, 10.45 GHz), (2) the interfering RF signal is received during the receive time interval of the sensor, (3) the frequency of the RF signal transmitted by the sensor and the frequency of interfering RF signal have a difference frequency that is a multiple of the pulse repetition frequency of the transmitted frequency signal, and (4) the RF interfering signal has a sufficient amplitude to produce an interfering noise signal.

These four conditions may be restated as follows, where RF1 represents the main sensor's RF centre frequency, RF2 represents the interfering sources RF centre frequency, IF1 represents the intermediate frequency (Generally, in some cases, such as in communications and electronic engineering, an intermediate frequency (IF) may be considered a frequency to which a carrier frequency is shifted as an intermediate step in transmission or reception) of RF1, and IF2 represents the intermediate frequency of RF2:

(1) Interference may occur when RF2 is within the demodulation frequency range of RF1, typically by +/−25 MHz;

(2) Interference may occur when the pulse repetition frequency of RF2 (PRF2) is a multiple of the RF1 frequency. More specifically, if RF1=RF2+/−n(PRF2), where n is any integer;

(3) Because the receiver is a synchronous phase detector interference may occur when the information on demodulated RF2 includes the frequency of IF1 or any of its odd harmonics. Stated another way, RF2 (i.e., a signal which has been modulated by AM/FM modulation, or any other modulation scheme) contains information on the IF1 or its odd harmonics;

(4) Interference may occur when RF1 and RF2 are combined and then subsequently demodulated, where RF2 is of sufficient signal level to produce a baseband noise component.

To curtail such baseband noise interference, the present technology contemplates implementation of several solutions. First, the sensors may be synchronized in time to avoid any overlap in RF pulses in time. Second, the sensors may be synchronized to avoid overlap in RF pulses in frequency (i.e., RF1=RF2+/−(n+0.5)(PRF2)). Third, the sensors may be configured to pulse in such a way that the probability of interference is negligible. Fourth, two or more sensors may be placed in one housing facing in different directions (e.g., placed midway along the bed at the headboard or at feet). Examples of each of the implementations are detailed herein.

For the case of a range gated RF sensor using a DRO as a reference oscillator, a second or subsequent sensor can have such a stable emitted frequency and behaviour, that it becomes a nearly optimal interferer to similar sensors that are nearby (i.e., when considering a multiple non-contact range gated sensor system).

In order to mitigate this interference for effective low noise operation where more than one sensor is in proximity the following implementations may be made:

(i) timing synchronization can be implemented between the sensors via a wire or wirelessly (where precise timing signals are used between cooperating sensors), or (ii) each sensor can be configured to independently behave in a manner that does not cause this nearly perfect interference (without requiring cooperation).

For the latter case (i.e., with no inter-sensor cooperation), dithering in both time and/or frequency may be used. Dithering of timing may be used to spread the noise, while frequency dithering may be used to prevent interference. For example, as discussed in more detail herein, in some embodiments ramping of the voltage on a diode coupled to a timing oscillator can change diode capacitance. This leads to a change in the frequency of oscillation of the timing oscillator, resulting in timing dithering, such as by dithering timing pulsed involved in the generated pulsed RF signals. Additionally, by ramping the supply voltage of the DRO (Dielectric Resonant Oscillator), the frequency is changed resulting in frequency dithering (e.g., by ramping voltage 2.5-3.0-2.5V) of the RF signals.

3. Timing Synchronization

Figure 9:
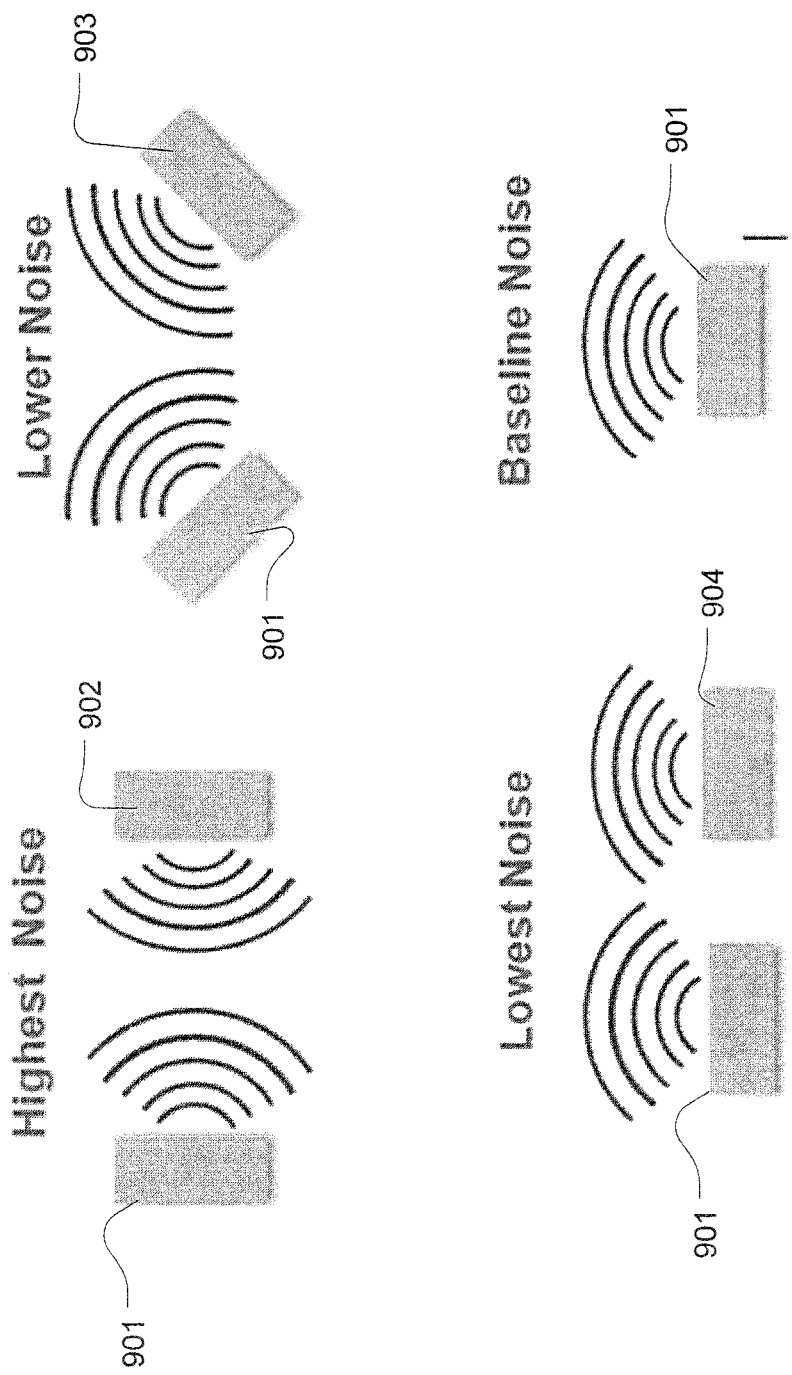
FIG. 9 is a diagram representation of sensor positions suitable for some embodiments of the present technology.

Time synchronizing of the RF pulses may be implemented by generating a synchronizing pulse from the first sensor (master) to the second sensor (slave). As such, the second sensor would transmit its RF pulse in the quiet period of the first sensor. This solution may have the same noise level as shown in the "baseline noise" setup of FIG. 9. Instead of by a master sensor, the synchronization of all sensors could be driven by an independent controller in a very similar way to that used by a master sensor to drive one or more slave sensors. Or indeed the sensors could act as peers, e.g., control and communication is distributed among devices in the field, whereby each device communicates directly with the devices around it without having to go through/via a master device.

In order to implement timing synchronization between sensors the following factors may be considered. First, the timing of the sensors may include synchronous dithering such as at a 1 ms interval, or more or less, so synchronization may not be easily achieved. Second, the timing of the sensors may be controlled by a ceramic resonator, with only about 1% frequency accuracy. Third, the slave unit should be enabled to detect loss of synchronization and maintain the sensor timing. Fourth, both a clock and dither synchronous signal can be transmitted from the master to slave sensor such as to help address issues of the use of dithering and the asynchronous nature of the operations. Fifth, synchronization should be achieved with sub-micro second timing accuracy to maintain the required RF pulse interleave locking. Sixth, the master and slave sensors should know they are required to transmit or receive the synchronization signal. (i.e., the sensors should automatically synchronize when required or be set at installation to synchronize)

3.1 RF Pulse Signal

Arising from these considerations, particularly in view of the dithering and asynchronous nature of the timing, some versions may include generation of a timing synchronization that includes transmission of both a clock and a dither synchronous signal, and which may be with sub micro second timing accuracy. There are a number of ways of achieving this, including detecting the RF pulse signal from the master unit. In this regard, when the pulse signal from the master unit is received by the slave units, the timing of the slave units are adjusted to assure the slave units do not transmit an RF signal at the timing associated with the pulse signal of the master unit. However, a change of timing architecture may be required as the RF pulse signal may not be at the clock frequency of the oscillator. Additionally, the implementation of a phase-locked loop (PLL) may be required but may be complicated by the dithering. If timing dithering is not employed then the synchronization requirements above are reduced to that of PRF pulse timing synchronization, which is a lesser requirement. Pulse timing dithering might not be employed and instead enhanced interference noise reduction may be achieved by RF frequency dithering in some cases.

3.2 RF Pulse Signal Detection at Intermediate Stage

Another method for transmitting both the clock and dither synchronous signal with sub micro second timing accuracy is by detecting the RF pulse signal of a master sensor at the IF (intermediate frequency) stage by the slave sensor. Because of circuit complexity to receive, amplify and condition the receive signal and in addition to phase lock it to the local 4 MHz oscillator, this solution is not easily implemented, however it is feasible, especially if digital sampling is employed.

3.3 Separate RF Signal

In another method, a separate RF synchronization signal may be sent. For example, a separate industrial, scientific, and medical band (ISM) RF signal may be generated to provide the synchronization signals from the master unit to slave units. In this regard, through a wireless means the ISM RF signal could potentially be piggy-backed on an existing RF communications channel.

3.4 Other Wireless Signal

In an alternate method, timing synchronization can be implemented through other wireless communications methods, including RF signals such as Bluetooth, Wi-Fi, ZigBee or other proprietary wireless means.

3.5 Infra-Red Signal

Figure 12:
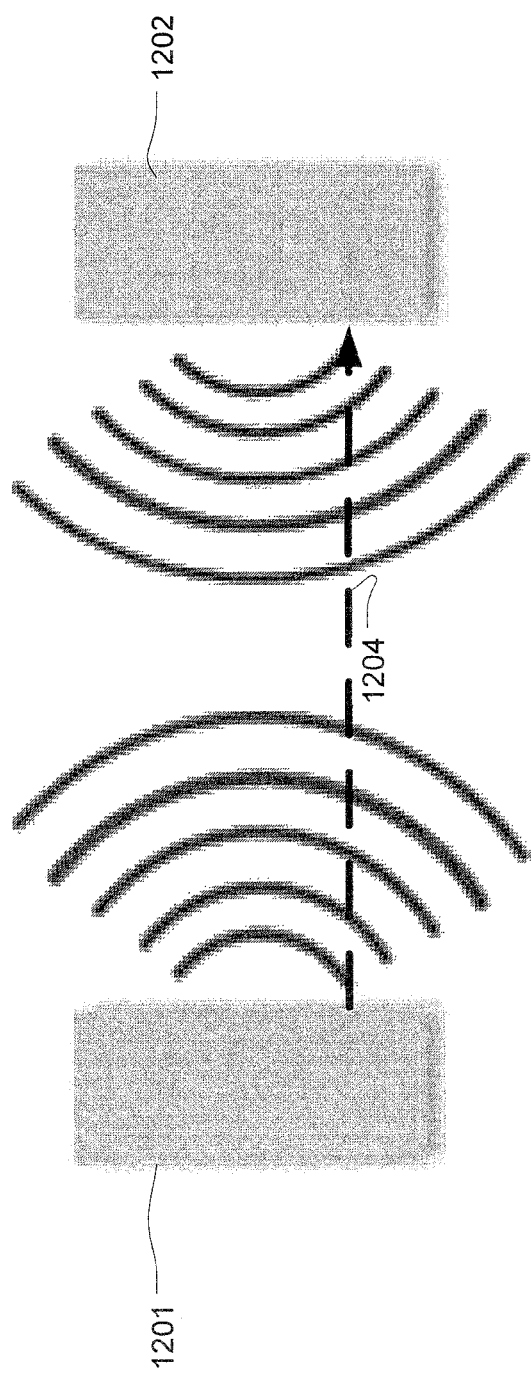
FIG. 12 is a diagram of an IR-Signal timing connection suitable for some embodiments of the present technology.

In an alternate method, timing synchronization can be implemented by photonic means such as through light pulses and specifically through an infra-red signal. As shown in FIG. 12, a master sensor 1201 could send an infra-red signal 1204 to slave sensor 1202. In this regard, the master sensor 1201 may include an infra-red transmitter/receiver and the slave sensor 1202 may include an infra-red transmitter/receiver. Accordingly, the master sensor 1201 may transmit timing signals from the infra-red transmitter to the infra-red receiver of the slave sensor 1202. However, complications achieving the required coverage and speed required for timing accuracy may be presented. For example, depending on the distance between the sensors, the infra-red signal may be delayed, thereby not providing proper synchronization. Further, interference issues such as a high speed IR signal "jamming" output from other devices (e.g., a television remote control) may be encountered. Other methods, such as fibre optic connection or transmission via visible light communication (e.g., pulsing LEDs or fluorescent lamps) in the range between 400 and 800 THz (780-375 nm) could also be used.

3.6 Wire Cable Coupling

Figure 13:
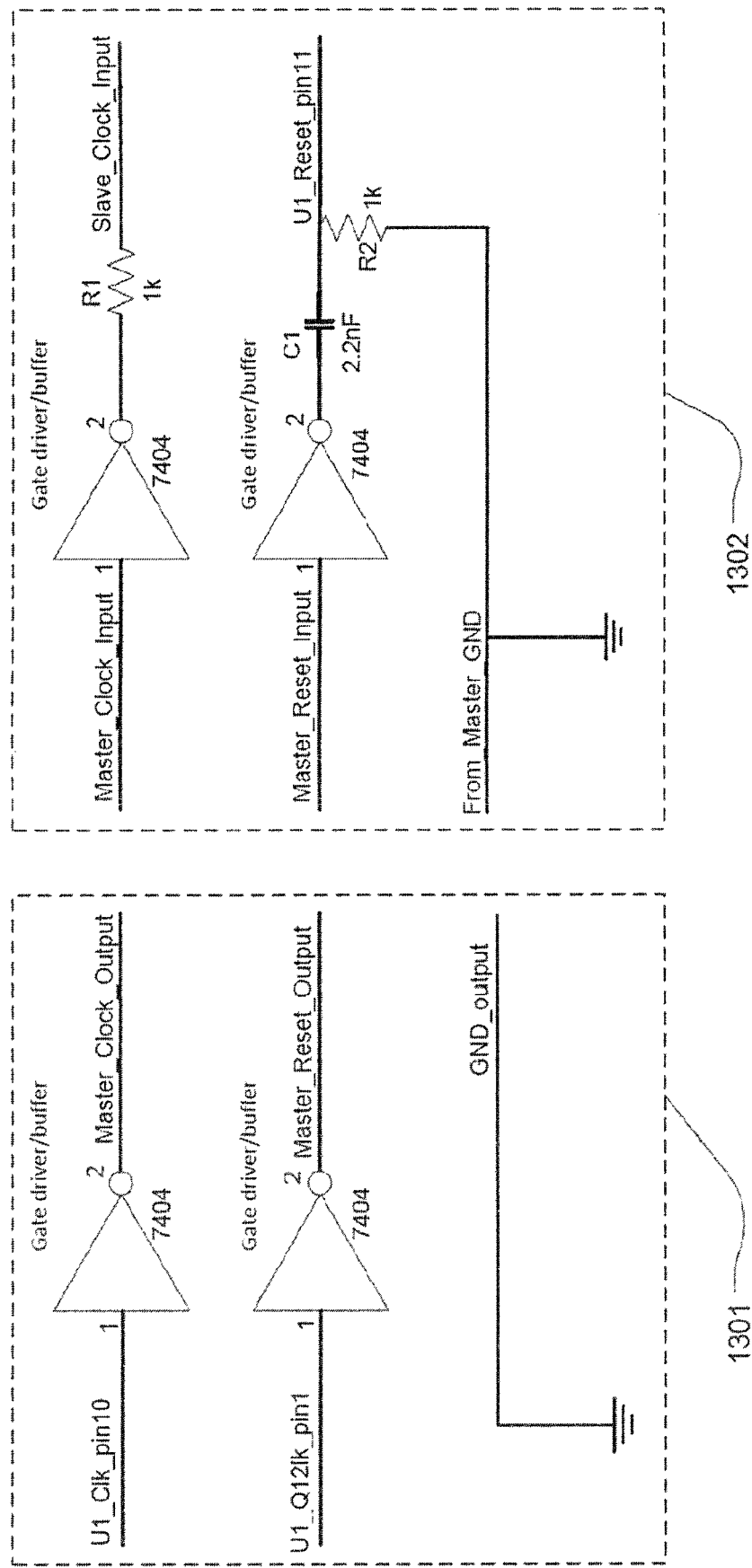
FIG. 13 is a three wire synchronous master slave test circuit as used in some embodiments of the technology.

Another method of timing synchronization can be implemented through a wired connection. For example, a multi-wire cable (e.g., a three wire cable or a two wire cable, etc.) may be used to connect a master sensor to a slave sensor. Such a three wire cable synchronous master-slave oscillator circuit is shown FIG. 13. The three wire cable may connect the master sensor to a slave sensor, thereby enabling the master sensor to transmit timing and dithering synchronization information from the master sensor to the slave sensor. On the left side of FIG. 13 is the master sensor circuit 1301, and on the right side of the figure is the slave sensor circuit 1302. The master sensor circuit may include a Reset U1 pin 11 connected to ground via 1 k resistor to enable reset control (not shown). Additionally, the master sensor circuit 1301 may include a 4 MHz oscillator input U1 CLK pin 10 buffered by a gate driver/buffer (and supplied as a clock output to the slave). Further, the master sensor circuit may include a 1 kHz dither output U1 Q12 pin 1 buffered by gate driver/buffer which is supplied as a reset output to slave. Finally, the master circuit may be connected to ground (0V) and supplied as output to the slave sensor.

The slave sensor circuit may include Reset U1 pin 11 connected to ground via 1 k resistor to enable reset control, as well as a 1 kHz dither output, received from the master circuit, and presented to the slave circuit Reset U1 pin 11 via 2.2 Nf series capacitor. The slave sensor circuit may further include a 4 MHz oscillator output gate driver/buffer received from the master circuit to drive transistor Q1 collector via a 1 kHz resistor. Finally, the slave circuit may include a circuit ground (0V) supplied as input from the master circuit.

In more general terms, the master clock output is transmitted through a first buffer (on the master circuit) to a wire which is received by a second buffer on the slave circuit. The output from the second buffer is presented to the slave clock input. Similarly the reset output is transmitted through a buffer to a wire which is received by a buffer on the slave circuit. The output from the second buffer is presented to the reset pin through a differentiator circuit/high pass filter. Only the leading edge of the reset pulse is passed through to the reset pin. The slave circuit may be connected to ground.

The master and slave sensors may be synchronized by a three wire cable by sending, from the master sensor, a pulse width of around 0.5 us for example. Such a pulse width enables out of phase synchronization of the RF pulses.

As already stated, if timing dithering is not employed then the synchronization requirements above are reduced to that of PRF pulse timing synchronization which is a lesser requirement. In this case the three wiring timing circuit described reduces to that of a two wire timing circuit. A two wire circuit can be implemented by transmitting the master reset output and letting the clocks run. This removes the master clock requirement.

A wired connection can achieve synchronization requirements and can also optionally provide other functions. For example, the wire cable could be implemented to power a second (or subsequent) unit(s). As such, the wire may allow for more remote sensor placements while not necessarily introducing more wires and cables. In addition the two wires could provide timing synchronization and power to a second unit by modulating the signals. The wire could also reduce the need for other wireless chipsets; e.g., a set of sensors may form a pair, with only one of them having a Wi-Fi or Bluetooth interface and power adaptor or space for batteries, and the second simply connected via cable and not having a need of a separate Wi-Fi etc. radio capability as relevant control/sensor data are also modulated onto the wire. A more complex wired connection based on Ethernet could also be used.

Both the three wire and two wire synchronization circuits described above could be implemented on the circuitry of the sensor or could be located in the connecting wires. The advantage of the latter would be that synchronization circuitry and associated cost would not be included in every unit.

3.7 Quartz Crystal

Either in addition to the above timing synchronization solutions, or as a standalone solution, the oscillator may be implemented with a quartz crystal. Accordingly, less frequent synchronization signals will be necessary as the quartz crystal has a high frequency tolerance and low frequency drift rate. Additionally, only a single synchronization signal is necessary (e.g., clock), as a quartz crystal may be implemented without dithering.

4. Frequency Synchronization

Another implementation to reduce RF interference between multiple sensors is to synchronize the RF frequencies of the sensors. In this regard the sensors can coexist without producing RF interference. For example, if two sensors transmit at RF frequencies, f1 and f2, respectively at time t, the receive signal due to f1 and f2 is:

$$A\cos 2\pi f_1 t + A\cos 2\pi f_2 t = 2A\cos 2\pi \frac{f_1 - f_2}{2} t \cos 2\pi \frac{f_1 + f_2}{2} t$$

Maximum interference between f1 and f2 occurs when $f_1 - f_2 = n*PRF \pm IF$, wherein IF is an intermediate frequency, and n is an integer. Minimum interference occurs when $f_1 - f_2 = (n+0.5)*PRF \pm IF$.

4.1 Differing Frequencies

To minimize interference, different sensors may be configured for different frequencies. In this regard, sensors may be dynamically set to different frequencies. For example, the sensors may implement a DRO whose frequency is a function of voltage. For example, a variation of 1V DC may result in an RF frequency change of 1.5 MHz.

The voltage controlled RF oscillator of the first sensor may synchronize to the RF frequency to the second unit. In this regard, a control circuit within the first sensor can adjust the DRO voltage to a minimum noise voltage by detecting the DRO voltages which result in a high level of interfering noise and by moving to a central control voltage position (i.e. an area of low noise) between these two "high noise level" voltages (e.g., where there is a pattern of constructive, destructive, constructive, destructive etc. interference gives rise to multiple interference maxima. RF frequency synchronization between two sensors has been demonstrated to produce the same noise level as if only a single sensor was in use.

4.2 Automatic Detection of Interference and Communication Between Sensors Via a Wired or Wireless Network, or Via Coded Interfering Pulses Another way of minimizing interference is by having each of a plurality of sensors detect their own respective centre frequency. Each sensor may then transmit their respective frequency value to the other sensors over a wired or wireless connection. The sensors may then adjust their respective centre frequencies to achieve an optimal spacing in order to maximally reduce interference between each other. In this manner, the more than one sensors can cooperate to reduce or avoid interference. Such a configuration may avoid the need to transmit a clock signal, clock edge, and/or a reset. Also this approach may be tolerant of delays and other potential issues that may arise in a communications channel, thereby allowing the sensors to operate over a link with poor quality of service (QoS). However, such an approach is not limited to poor QoS networks, and could be implemented on QoS links with good or high quality. Further, transmitting respective centre frequencies could potentially avoid the use of buffer circuits (unless required), dedicated cables, and/or synchronize radio or infra-red links. In contrast, transmitting a clock signal, clock edge, and/or reset constantly between sensors may require a defined QoS including latency, bandwidth, and other parameters. A network such as the Internet or an ad-hoc peer to peer Wi-Fi link such as Wi-Fi Direct using Wi-Fi Protected Setup (WPS) are examples of such a link (e.g., these are examples of links suitable for centre frequencies transmission or for a clock signal transmission).

Detection of a centre frequency may require a few additional circuit components amount of circuitry (e.g., tapping a signal from the mixer), and may be enabled by a digital sensor. In this regard, a first digital sensor may send a notification of its most current or recent centre frequency reading, to a second digital sensor, and the second digital sensor may send its most current or recent centre frequency reading to the first sensor. For example, the first digital sensor may send a centre frequency of 10.252791 GHz and the second digital sensor may send a centre frequency of 10.525836 GHz. The first and second digital sensors may then adjust their respective centre frequencies to achieve an optimal spacing, of for example, 125 kHz, in order to maximally reduce interference between each other. The optimal adjustment amount may be based on the IF and PRF configuration of the respective sensors. Although a digital sensor is described, transmittal of a frequency value may also be enabled by an analogue baseband sensor configured to share information with a processor in an attached device.

Transmittal of the centre frequencies may occur over a Wi-Fi, Ethernet, Bluetooth, or any other type of connection. Transmission may involve an authentication handshake and then periodic transmission of centre frequency values. Optionally, transmission of updated values may occur when the values deviate by a defined threshold from a past value. In some embodiments the transmitted data may be encoded in packets over the Wi-Fi link.

4.3 Frequency Lookup Table

Another technique to establish frequency synchronization is to use lookup tables of frequencies in each sensor. In this regard, sensors may each store copies of lookup tables (or functions or formula to dynamically calculate such frequencies). For example, a table or tables may include a set of odd frequencies and a set of even frequencies. The odd and even frequencies may be chosen to sit at nulls in mutual interference. The sensors may then be programmed to select a frequency to operate at from the odd and even tables. As such, the tables may span a region within an allowable spectral mask of a filter associated with a sensor, wherein the region is within the controllable centre frequency range of the sensor. For example, the frequencies may be selected from:

$$(0.5+n)*PRF;$$

Where n is an integer and PRF is a pulse rate frequency. In the case where sensors may be programmed to calculate frequencies using a mathematical formula as needed, such a configuration may permit a reduction in sensor memory.

In certain embodiments, a first sensor might check if it is operating at or near a frequency in either the even table or the odd table, and make minor adjustments to match one of these close (or closest) frequencies on either table. For example, the first sensor might adjust its frequency to the nearest frequency in the even table. A second sensor may then adjust its frequency to the nearest frequency in the odd table, thereby achieving minimal interference.

Communication between a defined pair (or plurality) of sensors may only have to happen once at setup. As such, a defined pair configuration may help remove the need for an ongoing wired or wireless transmission between the sensors. Accordingly, complexities introduced by continually updating the frequencies during ongoing operation may be minimized or removed.

The one-off pairing process for a defined pair (or plurality of sensors) could be performed via wired or wireless means. For example, near field communications (NFC) and/or an accelerometer could be used to enable "tap to pair," whereby close proximity and/or a control signal is used to enable the communication of the table information between sensors.

Alternatively, the pairing process could be repeated periodically, such as on an occasional or best effort basis (e.g., via a store and forward network) in order to verify that no control parameters have changed. In this regard, a change of location or situation of one or more sensors could cause a system to prompt a user to perform a manual re-pair, or the re-pairing process may be automatically performed in the background.

Where two or more sensors are in close proximity, parts of each table may be ring-fenced for each respective sensor. For example, each sensor may be assigned to a range of possible frequencies on the even table, or to a range of possible frequencies on the odd table. Additionally, there may be a switch, or some other type of input, on a sensor to define a preferred behaviour. For example, the switch may be set to adjust which frequency the sensor will operate at, or to select whether the sensor will operate at frequencies of the even table or the frequencies of the odd table or some portion thereof.

It also may be desirable that other metrics of the RF environment be collected by one or more sensor devices of the system. For example, other metrics of the RF environment which may be collected could be the spacing or a measure of distance between the sensors and the relative orientation of the sensors. Using these metrics, a configuration may be programmed such that the sensors cooperate in order to minimise mutual interference. Should the sensors be placed in a position where an elevated level of residual interference is likely, before or after a pairing routine is performed, the sensors may provide a notification to reposition or re-orient one or more of the sensors.

4.4 Detection of Friend or Foe

As noted, there are cases where multiple sensors, such as two or more, are in proximity and can interfere strongly with each other if countermeasures are not taken. However, even though the sensors can interfere, they are "friends" in that they can be configured to have specific behaviours when detecting and adjusting to interference from each other. In contrast, third party sources of RF signals may interfere with the operation of a sensor by accidentally or actively jamming the pulse sequences. Such third party sources operating at a similar centre frequency to a sensor may be considered "foes"; examples could be a sensing technology from another manufacturer or supplier operating at a similar frequency/pulsing strategy, or perhaps a malicious user trying to deliberately disrupt the operation of a medical cardiorespiratory sensor. Other exemplar sources that could interfere may be an in-bedroom/in-hospital (or outside bedroom) combined passive infrared sensor (PIR) and microwave security detector (e.g., where the microwave detector component operates at a similar RF centre frequency), a high power aviation RADAR, and/or a military, police or traffic management or vehicular RADAR may all produce similar centre frequencies which could interfere with operation of a sensor.

For the case of interference caused by friendly sensors, the sensors may be programmed to deliberately scan a frequency range to determine the presence of interference. In that regard, one or more of the friendly sensors may each modify its centre frequency, in a search mode to attempt to maximise interference. Upon maximising interference, the sensors may then reconfigure their centre frequency to minimise interference. A frequency range between the maximised and minimum interference frequencies may then be determined by the sensor(s). The sensors may then determine if the frequency range is related to, for example, a known frequency range, and if so, the sensors may assume that another sensor of a known type is the source of the interference. Such scanning would preferentially occur during the absence of any motion in the vicinity of the sensors.

Based on the determination that a friendly sensor is the source of interference, the sensors may initiate communication (e.g., using Manchester coding). For example, one or more of the sensors may adjust their respective centre frequencies around a determined interference maximum until two or more sensors agree upon the maxima. In this regard, a first sensor may move its centre frequency at a predefined rate, with the second (or plurality of other sensors) detecting when an interference maxima is achieved. Each sensor could communicate an agreed upon maxima point, and then agree which sensor should move to seek a minima frequency point. Upon achieving the minima, the sensor which adjusted to the minima would hold at that centre frequency until a correction is needed, for example, to account for temperature drift or other changing factor.

Such cooperative actions between friendly sensors may be made through base stations, and/or through mesh network of devices. In that regard, sensors may be reconfigurable, e.g., have the ability to dynamically adjust centre frequency by, for example, including a processor that controls varying voltage to a voltage controlled oscillator for example, and/or other RF characteristics including pulse timing and radiated power. In another embodiment, coding may be applied to some RF pulse trains to enable faster communication between "friends" without using other communications channels.

Therefore communication of a polling event to local or remote processor using a control signal is enabled in order to account for brief interfering signal and mask out. As such, this realises a system with no inter-communication needed (i.e., exact knowledge of current centre frequency is not needed). Thus, a temperature variation reference, e.g., detection of a certain temperature change, may be used to trigger or initiate polling between the sensors for updating the frequencies of each sensor to avoid interference as a result of recent temperature changes.

Figure 15:
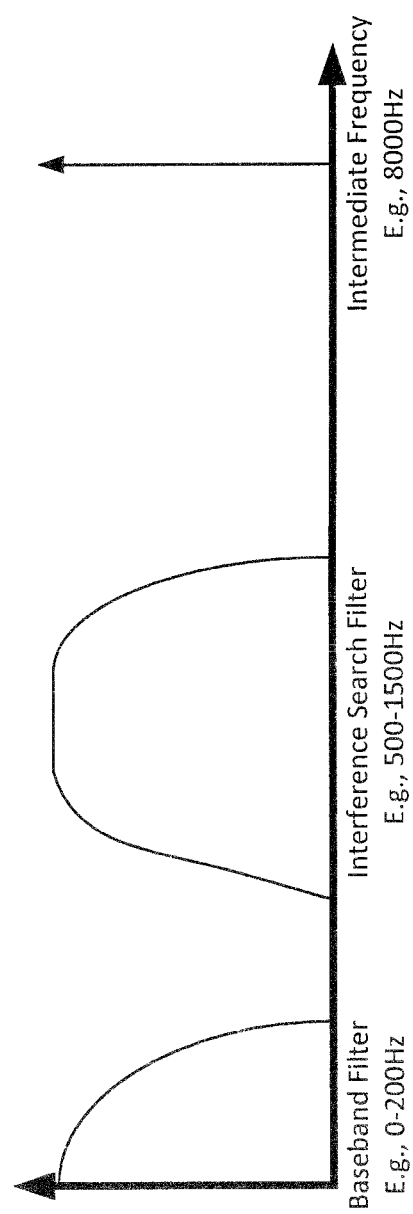
FIG. 15 shows a sample ratio between a sensor baseband range, an intermediate frequency and a filter range.
Figure 16A:
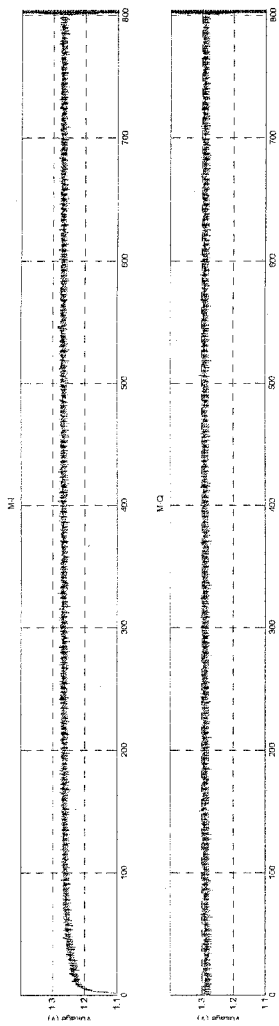
FIG. 16A is a signal graph with exemplar in-phase and quadrature baseband signals in the time domain with no interference.
Figure 16B:
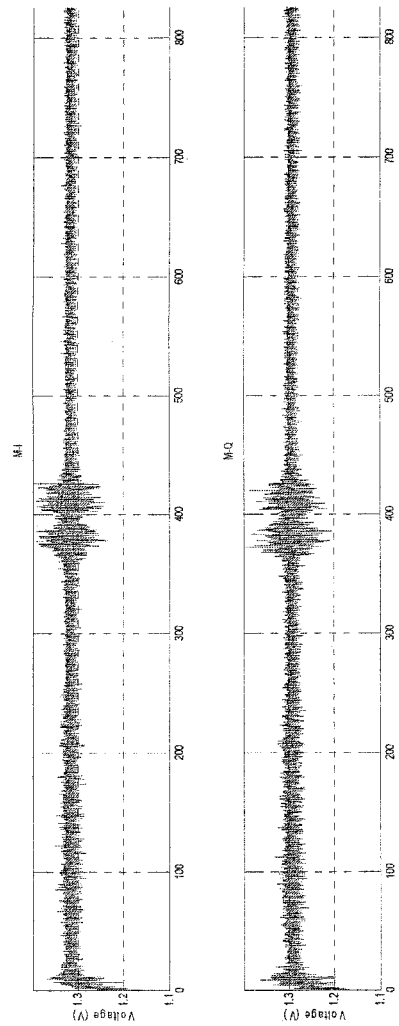
FIG. 16B is a signal graph with an intermittent interfering signal.
Figure 16C:
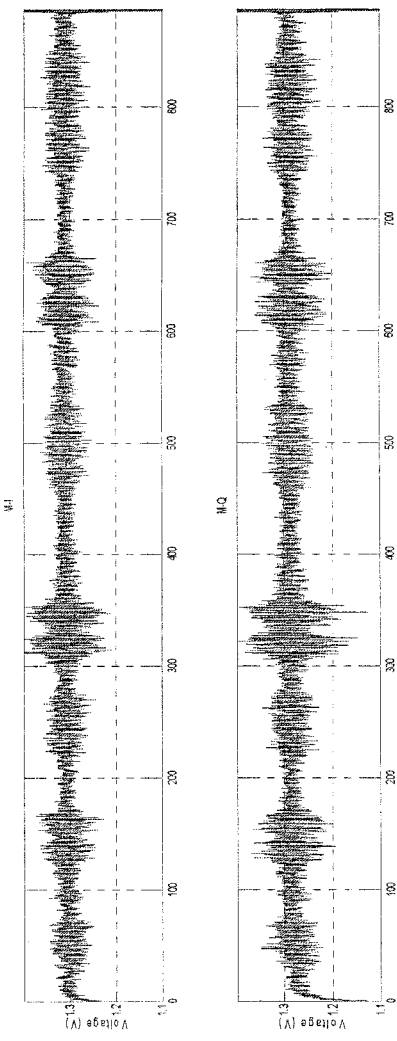
FIG. 16C is a signal graph with peak noise greater than 200 mVrms, where the timing of the peak noise level is unpredictable.

Based on the maximum interference detected and a sensor's own centre frequency, it is possible to measure the frequency of the interference signal. How this works is by (a) knowing the centre frequency of the sensor, (b) optionally sweeping the centre frequency, (c) locating maximal interference, and (d) deducing the frequency of this interfering source. Where maximal (or high/elevated) interference is detected, it can be deduced that the interfering source has a component at that frequency. Once the interfering frequency is known, it is possible to reconfigure the sensor, alert the user, or indeed reconfigure the third party interfering source (e.g., for the case where configuration of the third party sensor(s) is possible, such as by turning off, adjusting angle, distance, frequency, power level etc.). Maximal interference is defined by maximal noise; this can be measured by looking at the higher frequency components in the baseband or intermediate frequency. For the example of a sensor with baseband range from DC to 200 Hz, and intermediate frequency of 8 kHz, a filter range to check for interference could be say 500-1500 Hz (roughly, they are factors of 10 apart; one centred around the 100, one around the 1000, one approximately around the 10,000) (see FIG. 15). FIG. 16A shows exemplar in-phase and quadrature (IQ) baseband signals in the time domain with no interference. FIG. 16B shows an intermittent interfering signal, which 16C shows to have peak noise greater than 200 mVrms and unpredictable of the peak noise level.

4.5 Adjustment of Centre Frequency to Avoid Foes (or Other Interfering Sources)

As previously described, strong interference sources which are not from other sensors (i.e., friends), may be considered foes. A foe may transmit a RF signal with a centre frequency close or identical to the frequencies being transmitted by the one or more sensors. Accordingly, it is desirable for sensors to be able to operate in the presence of foes which may transmit jamming signals or other malicious RF emissions.

In some embodiments, the continued detection of an RF interference, caused by a foe, by a sensor cooperating with another sensor or sensors, may prompt a system to adjust the frequencies within which it is operating. For example, the system may carry out a search across an allowable lookup table of values or other allowable blocks of radio spectrum in order to find a situation such that the unusual external interference is minimised. If the third party source was a sensor using a similar pulsing scheme, it can be seen that moving to a null interference frequency (e.g., moving centre frequency by 125 kHz might be sufficient to minimise interference, and/or by adjusting PRF). If this was unsuccessful, it can be seen that a sensor could adjust centre frequency in steps in order to build up a picture of the local RF environment, and carry out an optimization process (e.g., using gradient descent interference avoidance) in order to locate an interference minima over time. In some examples, this may require a large change in centre frequency, such as, for example, a move from 10.587 GHz to 9.3 GHz (or vice versa).

Should the system be unsuccessful in minimizing the external interference caused by foes and/or other sources, the system may inform a user. For example, the system may attempt to adjust operation via clocking, transmission of adjusted centre frequencies or centre traversal via a special lookup table. If such adjustments are unsuccessful, the system may inform the user that a readjustment is "Unsuccessful," as residual interference detected is such that it exceeds a predefined acceptable threshold. Optionally, such information can be presented to the user only if the interference is sustained in nature. In certain extreme cases of interference, the sensor's RF radio may be turned off automatically, and an error signal set (e.g., displayed on a screen). As such, the sensor may be unable to process and/or extract physiological signals, and thus unable to detect user's biometric parameters. Further, if detected, the biometric parameters may be inaccurate.

5. Noise Reduction without a Synchronization Requirement

In some embodiments, noise reduction may be achieved without synchronization between two or more sensors. In that regard, the sensors may be configured to minimize RF coexistence issues without synchronizing the frequency or timing of the sensors.

5.1 Reduce RF Pulse Width

One such technique may include reducing the RF pulse width to lessen the probability of interference. Turning back to FIG. 5A, pulse width r may be used to determine the length of the RF pulse signals. Reduction of the pulse width while maintaining the pulse repetition interval, PRI, may have no adverse effect on the sensor operation. Additionally, the shorter pulse width has less chance of being modulated with other pulses than do longer pulses. The lowest pulse width value may be chosen to meet regulatory approval standards requirements for the RF signal bandwidth and spurious signal level.

5.2 Dither Each Sensor

Another technique for noise reduction may include dithering the pulse timing of each sensor differently or maintaining the pulse timing of each sensor at a constant frequency offset to each other. In this regard, the different timing from a master and slave sensor could reduce the chance of the sensors RF pulses locking in-phase with each other.

5.3 Increase Dither Timing

The pulse timing dither between two sensors may also be increased and made pseudo random to reduce noise. Similar to dithering the time of each sensor, the dithering cycle could be extended and made pseudorandom for either, or both, the master and slave sensor. In some examples, a second binary ripple counter and exclusive OR gate, or a microcontroller or processor may be used to create the extended and pseudorandom dithering cycle. As stated already, the synchronous nature of the dithering or pseudo random timing dithering with the PRF (and IF) is significant so that tone artefacts are not produced by the phase sensitive demodulator receiver of the sensor. In one example, a diode may be coupled with a timing oscillator (e.g., pulse generator 408 of FIG. 4) configured to control emission of timed pulses from the DRO. The voltage level on the diode may be ramped up, thereby changing the diode capacitance. This leads to a change in the frequency of oscillation of the timing oscillator. As such, timing dithering may occur.

5.4 Dither the RF Frequency

Another technique for asynchronously reducing the noise and interference is to dither the dielectric resonant oscillator (DRO) RF frequency to mitigate PRF frequency locking. Further, frequency dithering has the advantage of mitigating external RF interference. In some examples, an additional circuit to either modulate the drain voltage of the DRO or dither the supply voltage of the DRO from a voltage controlled regulator may be required. In this regard, by ramping the supply voltage of the DRO, the frequency output by the DRO may be adjusted.

Frequency dithering may allow for multiple sensors to coexist in a common vicinity. For example, by employing frequency dithering, the center frequency of each sensor is moving such that there is a statistically insignificant chance that interference occurs between the sensors in normal operation. Such a technique may also be utilized by itself or in addition to timing dithering.

5.5 Single Housing

Figure 14:
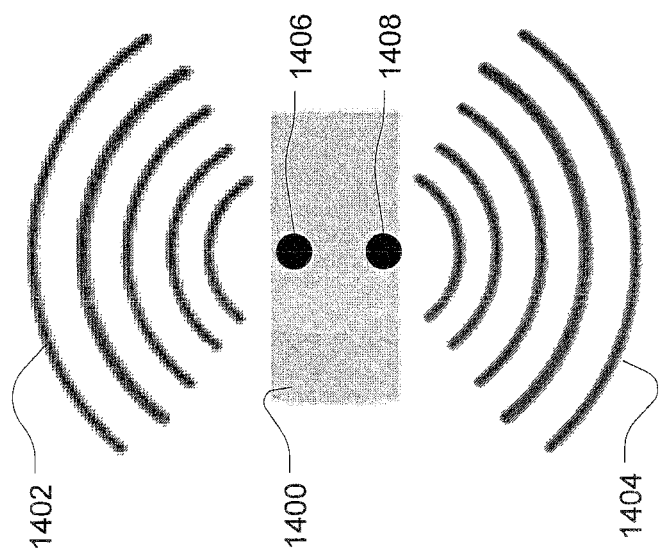
FIG. 14 is an example of housing suitable for some embodiments of the technology.

Another technique for reducing noise between sensors is by positioning the sensors in a single housing unit. As shown in FIG. 14, two sensors 1406 and 1408 are placed within housing unit 1400. Sensor 1406 is placed 180 degrees away from sensor 1408, and accordingly signals 1402 and 1404 create minimal, if any, interference. Turning back to FIG. 9, the lowest level of noise between sensors occurs when the sensors are placed at least 90 degrees apart. Accordingly, when placing the sensors within the housing, they should be at an angle of at least 90 degrees from each other. A benefit of this technique is the sensors can be easily synchronized through a direct connection.

5.6 Orientation

Because the signal level of the interference source is important the location of the sensors has a role to play in reducing noise. Placing sensors in close proximity and in a line of sight of each other produces maximum interference noise. This noise can be mitigated by orienting the sensors to increase the effective path length. Locating sensors further apart and at an angle to each other is an effective means of reducing coexistence noise

5.7 Polarisation

When the sensors transmit and receive RF signals are circularly polarised (i.e., their RF signal electric and magnetic fields have a preferred transmit and receive direction) then further noise reduction can be achieved by arranging the sensors such that the polarisation of one sensor is orthogonal to that of the other. In this way the reflected movement signal is preferred (suffers no attenuation due to polarisation) while the received interference RF signal is rejected (suffers attenuation due to its orthogonal polarisation).

6. Combination Configurations

Noise reduction may also be obtained by using more than one of the previously described noise reduction architectures and/or techniques. In Table 1 below: "S" represents Synchronization and "D" represents Dithering. For the case of a term in brackets "( )", this implies the case of "S" and/or "D" (i.e., to simplify the presentation of Table 1). For Table 1, "t" represents Timing (which includes IF timing and PRF timing). "f" represents the RF centre frequency. "nothing" represents where no intervention is made (i.e., noting/nothing is the trivial as-is case). Table shows the case of 1 co-existing sensor, but could be extended to (1, 2, . . . n) linked sensors. It should be noted that synchronization of timing implies the synchronization of a wired or wireless control signal (i.e., a first control signal); if dithering is also employed (simultaneous synchronization of timing and the dithering of timing), then a second control signal is used to facilitate synchronization. For timing synchronization, this implies that the PRF timing are locked. For dithering, this implies that IF and PRF are synchronised, but dithered (hence the requirement for the second control signal).

A potential limitation of timing synchronization alone is that it requires good RF pulse isolation. (RF bleed through of the RF signal during the OFF period of the RF modulation results in poor RF pulse isolation). Therefore, it is desirable to turn off the RF radio transmitter between pulses or other approaches to remove this bleed through.

In considering Table 1, the combination of timing dither and frequency synchronization [t(D) f(S)] is likely to perform well. The combination of timing synchronization and frequency synchronization [t(S) f(S)] is also likely to perform well, especially if there is good isolation, or timing synchronization and timing dither and frequency synchronization [t(S,D) f(S)].

TABLE 1

| t (of IF and PRF) | f |
|---|---|
| Nothing | Nothing |
| S (D) | Nothing |
| S (D) | D |
| Nothing | S |
| D | S |
| S (D) | S |
| D | D |
| D | Nothing |
| Nothing | D |

7. Other Considerations

7.1 Correcting for Temperature Variation

A centre frequency of a sensor may shift, even under the control of a DRO, as certain operating parameters change. In this regard, a variation in both ambient and internal temperature may cause a sensor's frequency output to shift. In some examples, sensors may experience repeated and significant changes in temperature if a high power light or heat source is in proximity of, or in the same housing as, an RF sensor, and such a source switches on or off over time. There may also be a shift in centre frequency when a product with a processor and sensor is first turned on, and the enclosure reaches the expected operating temperature of the system (which may be above ambient temperature).

For the case of a system that contains separate temperature monitoring, a detection of a change in temperature (with reference to rate of change in temperature over time) can be used to adjust the sensor transmission frequency. Therefore, embodiments may include design parameters to assist the sensor in outputting a certain frequency, regardless of any temperature variations.

For a system with two or more sensors sending a continuous clock or associated reset synchronization signal over wired or wireless link with defined QoS, any temperature or related change in centre frequency may automatically be corrected. In this regard, the sensors may be adjusted by the techniques previously described regarding QoS.

For a system with two or more sensors sending periodic centre frequency values read from sensors, optimal spacing may be maintained. For example, the sensors may transmit the values read from the sensors over a network, which allows the adjustment of one or more sensors in such a way that defined frequency spacing is achieved and retained. As such, interference between sensors may be minimized. Such corrections may be made based on a change or delta in a centre frequency of a sensor above a defined threshold.

For a system with two or more sensors using lookup tables, subsequent to an initial pairing process, each sensor may be able to dynamically detect their current centre frequency (e.g., as drifting due to a change in temperature or other parameter), and continually or on a periodic basis adjust its frequency in order that it matches an agreed lookup table centre frequency. Such adjustments may thereby minimising interference between the sensors, while assuring the sensors remain within a defined spectral mask.

RF sensor variation and processor control offsets may also be used to estimate the temperature such that an RF sensor alone could be used to estimate temperature to a certain resolution. In this regard, the temperatures may allow for sensor start-up effects, and further, the resolution may enable temperature sensing where no separate temperature sensor is provisioned. Accordingly, no prior knowledge of a temperature coefficient of the oscillator may be necessary.

7.2 Reduce Sensor Synchronization Events

The amount of times a sensor may provide its actual centre frequency to nearby sensors may be reduced by reading and accurately setting the centre frequency at the time of manufacture. In this regard, it is possible to know the maximum and minimum extremes, in terms of temperature, with which a DRO or a quartz crystal operates. Based on the maximum and minimum extremes, it is also possible to determine a temperature coefficient, as operation of the DRO may be linear. Based on the frequency of operation being output by the sensor, an adjustment to correct for inaccuracies caused by the operating temperature may be made given the known temperature coefficient.

7.3 Third Party Timing Correction

In embodiments where a sensor measures its own centre frequency, the accuracy of the clock producing the RF signals may be known and adjusted for in the centre frequency determination. For example, a network time protocol (NTP) may be used to determine the actual frequency of the clock at a certain time. A timing calibration may then be performed on the clock, so the other sensors may be adjusted to assure they operate at previously defined differences in frequency. NTP is a networking protocol for clock synchronization between systems over packet-switched, variable-latency data networks (e.g., the internet, and using User Datagram Protocol (UDP) on port number 123).

Commercial crystals may have a known clock rate and accuracy. For example, a crystal may have an accuracy of 20 parts per million, and an associated variation with temperature. In cases of a slow temperature change, for example, a period of 10 or 30 mins, a timing calibration can be performed on the 4 MHz clock. In this regard, once the current time is available, it is possible to send to the other devices.

To provide the current time to other sensors, the clock rate, in this example a 4 MHz clock, may be mixed with a frequency rate, for example 10.525 GHz. As a result of the mixed signal, a harmonic of the 4 MHz clock signal appears on the received signal. Therefore, based on the output, there is a frequency that is:

$$n*\text{actual frequency}$$

Where n is an integer and where actual frequency is the outputted frequency of the sensor (in the current example 10.525 GHz). The clock rate, due to accuracy issues, may be slightly different than the advertised rate. Continuing the above example, the clock rate may be 4.01387 MHz. To assure an accurate timing between the sensors, the clock rate may be adjusted until the output frequency includes no frequency deviation and/or beat frequency. Based on the adjusted rate, the crystal can be determined to be operating at n times the clock rate.

Based on the passage of time using the network timing protocol or GPS timing signals or other time reference, a clock synchronization signal may be calculated. For example, a reference frequency may be found from an internet source. Based on passage of time using the NTP, a clock synchronization signal may be calculated. This synchronization signal may then be sent to the other sensors.

7.4 Location Aware Sensor Parameters

In some embodiments it may be possible for a sensor to obtain location information. In this regard, the sensor may include or have access to the data of a positioning system, such as a global positioning system (GPS), whereby the sensor may obtain geographical location information as to where the sensor is currently positioned. In some embodiments, the sensor may be included in, or connected to, a smart-device (e.g., smartphone, tablet, smartwatch etc.). Accordingly, the sensor may receive its geographical location information from that smart-device. Timing information may also be recovered via a GPS receiver, and could allow wireless synchronization (assuming that an adequate GPS signal is available).

Based on input of geographical location information, the sensor may then assure that its operation is within an allowed spectral mask for the current geographical region which the sensor is located. Alternatively, the sensor may automatically deactivate if possible control set of parameters of the sensor are incapable of operating the sensor within the allowed spectral mask of the geographical region which the sensor is located. Therefore, one or more sensors can coexist both with local radio frequency regulations and with one another.

7.5 Low Power State

Sensors may be switched to a low power search mode (or even a sleep or off mode) if no motion is detected for a predetermined amount of time. In this regard, a sensor might be integrated into body worn devices, such as pendants, chest bands, bracelets, watches, hats, and other such devices. Additionally, sensors may be directly into existing electronics devices such as, smart watches, smartphones, internet of things (IoT) devices, etc.

As such, sensors may be programmed to switch to a low power search mode if the device which the sensor is integrated is not being used, such as if no motion is detected. For example, a sensor integrated into a pendant may be placed onto a dresser. Since the user is not wearing the pendant, the sensor may detect no motion. Accordingly, the range of the sensor may be adjusted by reducing the output power, frequency, and/or duration of pulses to reduce the overall power consumption. Further, the adjustments may be programmed to be within allowable ranges. While sensors integrated into devices are described, standalone sensors may also be programmed to switch to a lower power search mode if the sensor fails to detect motion. Therefore, a low power condition can act a further aid to coexistence, by reducing the RF emitted power of one or more sensors.

7.6 Security

Sensors might also be used in security sensing applications, to detect unauthorised physiological patterns (e.g., intrusion of a person or persons) into a detection area, and raise an alarm (or send a control signal to processor). As can be seen, in a security application, many such sensors could be co-located in a building, and thus RF sensor coexistence is highly important. It is also possible that one or more sleep sensors could be reconfigured by a control system when the user is away during the day to act as nodes or sensors in an intruder (burglar) alarm system (e.g., to detect an intruder in a bedroom).

7.7 Processing

Processing of signals, such as those received by a sensor, may be performed by a processor on a sensor printed circuit board assembly (PCBA). Such a PCBA may also allow communication over an analog and/or digital link with a remote processor, such as a microprocessor on a main board.

In embodiments with digital sensors, signals may be digitized and transmitted over a wireless or wired connection. Digitisation may be performed at a high resolution and/or sampling rate, and the sensor signals themselves (e.g., in-phase (I) and quadrature (Q) streams, or a stream prior to or not requiring such separation of I and Q), may be transmitted to a single or multiple processors. Further, each channel of transmitted information may also contain information about current or recent centre frequency, relative changes in centre frequency, lookup table location in use, etc.

The number of components to implement a multi-sensor system may be reduced by minimising component count on one or more sensors. For example, in an operating environment, such as a home, apartment block, hotel, office, hospital or nursing home where multiple sensors are in use, the system may utilise existing data links and/or data processing power available in a wider system implementation in order to achieve the desired motion and physiological sensing. In one example, sensors may transmit their respective signals to a remotely located, separately housed processor, capable of processing multiple sensor signals at once.

Optionally, digitised sensor signals could be transcoded to audio frequencies such that existing audio processing accelerators and routines might be utilised in order to detect specific motion patterns.

In addition, whilst the main focus of the described technology is associated with applications for detecting respiration, sleep and heart rate, it is similarly suitable for detecting other movements of the human body (or of an animal if so configured).

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology. It will further be understood that any reference herein to subject matter known in the field does not, unless the contrary indication appears, constitute an admission that such subject matter is commonly known by those skilled in the art to which the present technology relates.

PARTS LIST detection apparatus 100
detection apparatus 102
sensor 300
sensor 302
RF pulse 310
RF pulse 312
sensor 402
oscillator 404
pulse generator 408
periodic sinusoidal amplitude envelope 600
signal 602
signal 700
signal 702
resultant receiver RF signal 704
sensor 800
second active source 802
object 804
rf signal 806
signal 808
master sensor 1201
slave sensor 1202
red signal 1204
master sensor circuit 1301
slave sensor circuit 1302
housing unit 1400
signal 1402
signal 1404
sensor 1406
sensor 1408

The invention claimed is:

1. A radio frequency physiological motion sensor configured for operation in a multi-sensor configuration, the radio frequency motion sensor comprising:

a radio frequency transmitter, the transmitter configured to emit pulsed radio frequency signals; and a receiver configured to receive reflected ones of the emitted pulsed radio frequency signals to detect motion of a reflecting surface; the transmitter and receiver configured to sense one or more physiological characteristics of a user comprising at least respiratory motion;

wherein the transmitter is configured for synchronized transmission of the pulsed radio frequency signals with another radio frequency physiological motion sensor in a vicinity of the radio frequency physiological motion sensor to mitigate interference between emitted pulses from the radio frequency physiological motion sensors.

2. The radio frequency physiological motion sensor of claim 1 wherein the transmitter is synchronized in time to interleave emitted pulsed radio frequency signals with emitted pulsed radio frequency signals of the another radio frequency physiological motion sensor.

3. The radio frequency physiological motion sensor of claim 2 wherein synchronization between the radio frequency motion sensors comprises transmission of a clock signal.

4. The radio frequency physiological motion sensor of claim 3 wherein the synchronization between the radio frequency physiological motion sensors comprises transmission of a dither synchronous signal.

5. The radio frequency physiological motion sensor of claim 3 wherein the radio frequency physiological motion sensor detects timing from an emitted pulsed radio frequency signal.

6. The radio frequency physiological motion sensor of claim 3 wherein the radio frequency physiological motion sensor detects a synchronization signal independent of the emitted pulsed radio frequency signals.

7. The radio frequency physiological motion sensor of claim 1 wherein the radio frequency physiological motion sensor further comprises an infra-red signal transmitter adapted for timing of the emitted pulsed radio frequency signals.

8. The radio frequency physiological motion sensor of claim 1 wherein the radio frequency physiological motion sensor comprises an interface for wired connection with the another radio frequency physiological motion sensor, the wired connection being configured for timing of the emitted pulsed radio frequency signals.

9. The radio frequency physiological motion sensor of claim 1 wherein the transmitter is synchronized with a transmitter of the another radio frequency physiological motion sensor with respect to frequency to reduce interference.

10. The radio frequency physiological motion sensor of claim 1 wherein the transmitter comprises a variable oscillator configured for frequency adjustment in response to detected interference noise.

11. The radio frequency physiological motion sensor of claim 1, wherein to mitigate interference between emitted pulses from the radio frequency physiological motion sensors the transmitted is configured to ramp dither timing of pulse generation using a synchronous ramp dithering circuit, wherein the transmitter is configured for frequency dithering.

12. The radio frequency physiological motion sensor of claim 1, wherein to mitigate interference between emitted pulses from the radio frequency physiological motion sensors the sensors are configured to ramp dither timing of pulse generation using a synchronous ramp dithering circuit, wherein the transmitter is configured for time dithering.

13. The radio frequency physiological motion sensor of claim 1 wherein the transmitter is configured to dither the frequency of the pulsed radio frequency signals.

14. The radio frequency physiological motion sensor of claim 1, wherein the radio frequency physiological motion sensor is a pulsed continuous wave radio frequency sensor.

15. The radio frequency physiological motion sensor of claim 1 wherein physiological characteristic motion is produced by modulating the received reflected radio frequency signals with the emitted radio frequency signals.

16. The radio frequency physiological motion sensor of claim 1 wherein radio frequency physiological motion sensor is configured to range gate the radio frequency signals.

17. The radio frequency physiological motion sensor of claim 1 wherein the physiological characteristics comprise one or more of cardiac activity and limb movement.

18. The radio frequency physiological motion sensor of claim 1 wherein radio frequency physiological motion sensor is configured to determine a phase difference between the emitted radio frequency signals and the received reflected radio frequency signals to sense any of respiration and cardiac activity of the user.

19. The radio frequency physiological motion sensor of claim 1 wherein the radio frequency physiological motion sensor is configured to couple to a respiratory treatment apparatus that provides an automated treatment response based on an analysis of the physiological characteristics detected by the radio frequency physiological motion sensor.

20. The radio frequency physiological motion sensor of claim 1 wherein the radio frequency physiological motion sensor is configured to inform a user of interference detected if it exceeds a predefined threshold.

21. A radio frequency physiological motion sensor for physiological characteristics sensing including at least respiratory motion, the radio frequency physiological motion sensor comprising:

a radio frequency transmitter, the transmitter configured to emit pulsed radio frequency signals; and a receiver configured to receive reflected ones of the emitted pulsed radio frequency signals to detect motion of a reflecting surface;

wherein the transmitter is configured with a dither timing different from a dither timing of another radio frequency physiological motion sensor in a vicinity of the radio frequency physiological motion sensor to mitigate interference between emitted pulses from the radio frequency physiological motion sensors.

22. The radio frequency physiological motion sensor of claim 21, wherein the dither timing of the transmitter is pseudo random.

23. The radio frequency physiological motion sensor of claim 21 wherein the transmitter is configured with frequency dithering.

24. A system for transmitting radio frequencies for physiological characteristics sensing including at least respiratory motion, comprising:

a master radio frequency physiological motion sensor; and a slave radio frequency physiological motion sensor;

wherein the master radio frequency physiological motion sensor is configured to transmit a first radio frequency (RF) signal; and the slave radio frequency physiological motion sensor is configured to transmit a second RF signal, wherein the system is arranged to minimise interference between the first radio frequency (RF) signal and the second RF signal.

25. The system of claim 24, wherein the slave radio frequency physiological motion sensor is configured to transmit the second RF signal such that the second RF signal creates minimal interference with the first radio frequency (RF) signal.

26. The system of claim 24, wherein the master radio frequency physiological motion sensor and slave radio frequency physiological motion sensor are placed within a single housing.

27. The system of claim 26, wherein the master radio frequency physiological motion sensor and slave radio frequency physiological motion sensor are positioned within the single housing at an angle of 90 degrees.

28. The system of claim 24, wherein an RF transmitter is configured to transmit at least one synchronization RF pulse signal.

29. The system of claim 28, wherein the slave radio frequency physiological motion sensor is further configured to receive the synchronization RF pulse signal.

30. The system of claim 29, wherein the slave radio frequency physiological motion sensor is further configured to detect the received synchronization RF pulse signal at an intermediate frequency.

31. The system of claim 28, wherein the master radio frequency physiological motion sensor is further configured to transmit the at least one RF pulse signal on a separate industrial, scientific and/or medical transmission band (ISM).

32. The system of claim 24, wherein:
the master radio frequency physiological motion sensor further comprises an infra-red (IR) transmitter configured to transmit an IR synchronization signal; and
the slave radio frequency physiological motion sensor further comprises an infra-red (IR) receiver configured to receive the transmitted IR synchronization signal.

33. The system of claim 24, wherein the master radio frequency physiological motion sensor and the slave radio frequency physiological motion sensor further comprise a master-slave oscillator circuit.

34. The system of claim 33, wherein the master-slave oscillator circuit further comprises a multi-wire cable interconnection configured to transmit timing and dithering synchronization information from the master radio frequency physiological motion sensor to the slave radio frequency physiological motion sensor.

35. The system of claim 24, wherein at least one of the master radio frequency physiological motion sensor and the slave radio frequency physiological motion sensor includes at least one resonator oscillator circuit.

36. The system of claim 35, wherein at least one resonator oscillator circuit includes a quartz crystal.

37. The system of claim 35, wherein the slave radio frequency physiological motion sensor includes the at least one resonator oscillator circuit as well as a voltage controlled RF oscillator, wherein the voltage controlled RF oscillator is configured to synchronize its RF signal frequency to the master radio frequency physiological motion sensor.

38. The system of claim 37, wherein the voltage controlled RF oscillator is configured to synchronize the RF frequency to the master radio frequency physiological motion sensor by detecting a high voltage which result in a high level of interfering noise, detecting a low voltage which result in a high level of interfering noise and moving the voltage controlled RF oscillator to a central control voltage position between the high and low voltage.

39. The system of claim 24, wherein at least one of the first radio frequency (RF) signal and second RF signal has an RF pulse width of about 0.5 μs.

40. The system of claim 24, wherein the master radio frequency physiological motion sensor is configured to provide a first dithering time to the first radio frequency (RF) signal; and
the slave radio frequency physiological motion sensor is further configured to provide a different dithering time to the second RF signal.

41. The system of claim 24, wherein the master radio frequency physiological motion sensor includes a first binary ripple counter and exclusive OR gate; and
the slave radio frequency physiological motion sensor includes a second binary ripple counter and exclusive OR gate;
wherein, the first and second binary ripple counter and exclusive OR gates are configured to create a pseudo random dithering time.

42. The system of claim 24, wherein the master radio frequency physiological motion sensor includes a first dielectric resonant oscillator, wherein the first dielectric resonant oscillator is modulated by a first voltage; and
the slave radio frequency physiological motion sensor includes a second dielectric resonant oscillator, wherein the second dielectric resonant oscillator is modulated by a second voltage.

43. The system of claim 24, wherein the first radio frequency (RF) signal and second RF signal are at different frequencies.

44. The system of claim 24 wherein both physiological motion sensors are pulsed continuous wave radio frequency sensors.

45. The system of claim 24 wherein both physiological motion sensors are configured to detect physiological characteristics by modulating received reflected radio frequency sensing signals with emitted radio frequency sensing signals.

46. The system of claim 24 wherein both physiological motion sensors are configured to range gate radio frequency sensing signals.

47. The system of claim 24 wherein both physiological motion sensors sense one or more of respiration activity, cardiac activity and limb movement.

48. The system of claim 24 wherein both physiological motion sensors are configured to determine a phase difference between emitted radio frequency sensing signals and received reflected radio frequency sensing signals to sense any of respiration and cardiac activity of a user.

49. The system of claim 24 wherein at least one of the two or more radio frequency sensors is configured to couple to a respiratory treatment apparatus that provides an automated treatment response based on an analysis of the physiological characteristics detected by the at least one of the two or more radio frequency sensors.

50. The system of claim 24 wherein at least one of the two or more radio frequency sensors is configured to inform a user of interference detected if it exceeds a predefined threshold.

51. A system for transmitting radio frequencies for physiological characteristics sensing including at least respiratory motion comprising:
a first radio frequency physiological motion sensor; and
a second radio frequency physiological motion sensor;

wherein the first radio frequency physiological motion sensor is configured to transmit a first radio frequency (RF) signal; and the second radio frequency physiological motion sensor is configured to transmit a second RF signal, wherein the system is arranged to minimise interference between the RF signals of both sensors.

52. The system of claim 51, wherein the first radio frequency physiological motion sensor is configured to receive an indication of the frequency transmitted from the second radio frequency physiological motion sensor, and the second radio frequency physiological motion sensor is configured to receive an indication of the frequency transmitted from the first radio frequency physiological motion sensor.

53. The system of claim 52, wherein the first radio frequency physiological motion sensor is configured to adjust the frequency of the first radio frequency (RF) signal in response to the received indication of the frequency transmitted from the second radio frequency physiological motion sensor.

54. The system of claim 51, wherein each of the first radio frequency physiological motion sensor and the second radio frequency physiological motion sensor is configured to access a lookup table which includes selectable frequencies at which the sensors can operate.

55. The system of claim 54, wherein the first radio frequency physiological motion sensor is configured to select a frequency from a first lookup table, and the second radio frequency physiological motion sensor is configured to select a frequency from a second lookup table.

56. The system of claim 55, wherein the first lookup table comprises odd frequencies and the second lookup table comprises even frequencies.

57. The system of claim 51, wherein the first radio frequency physiological motion sensor and the second radio frequency physiological motion sensor are configured to adjust their respective frequencies using a network time protocol (NTP).

58. The system of claim 51, wherein the first radio frequency physiological motion sensor and the second radio frequency physiological motion sensor are configured to adjust their respective transmission frequencies in response to detecting interference.

59. The system of claim 51, wherein the first radio frequency physiological motion sensor and the second radio frequency physiological motion sensor are configured to adjust their respective transmission frequencies based on predetermined temperature coefficients.

60. The system of claim 51, wherein the first radio frequency physiological motion sensor and the second radio frequency physiological motion sensor are configured to check or adjust the frequency at which they transmit RF signals in response to input of geographical location.

61. The system of claim 51, wherein at least one of the first radio frequency physiological motion sensor and the second radio frequency physiological motion sensor is configured to operate in a low power mode upon detection of an absence of motion.

62. The system of claim 51, wherein the first radio frequency motion sensor and the second radio frequency physiological motion sensor are configured to send a continuous clock signal over a wired or wireless link.

63. The system of claim 51, wherein at least one of the first radio frequency physiological motion sensor and the second radio frequency physiological motion sensor is configured to:
send periodic centre frequency values read from each respective sensor over a network; and
adjust the frequency at which each sensor transmits to minimise interference between the first and second sensors.

64. The system of claim 51, wherein at least one of the first radio frequency physiological motion sensor and the second radio frequency physiological motion sensor is configured to:
dynamically detect its respective current centre frequency; and
periodically adjust such frequency in order that it matches an agreed lookup table centre frequency so interference between the first and second radio frequency physiological motion sensors is minimized, while remaining within a defined spectral mask.

65. The system of claim 51, wherein the first radio frequency physiological motion sensor and the second radio frequency physiological motion sensor are configured so that:
a frequency range is dynamically scanned to detect minimum and maximum interference; and
a centre frequency of at least one of the sensors is adjusted to a frequency associated with the minimum.

66. The system of claim 65 wherein the sensors communicate via a frequency of maximum interference.

67. The system of claim 51, wherein at least one of the first radio frequency physiological motion sensor and the second radio frequency physiological motion sensor is configured to:
detect a temperature change; and
initiate polling between the sensors, based on the detected temperature change, for adjusting a centre frequency of at least one of the sensors.

68. The system of claim 51 wherein the system is arranged to minimise interference between the RF signals of both sensors by frequency dithering of one or more oscillators of the sensors generating the RF signals.

69. The system of claim 68 wherein a voltage level to at least one of the one or more oscillators is ramped to produce the frequency dithering.

70. The system of claim 51 wherein the system is arranged to minimise interference between the RF signals of both sensors by timing dithering of pulses of the RF signals of both of the sensors.

71. The system of claim 70 wherein a voltage level to a diode coupled with at least one of the one or more oscillators is ramped to implement the timing dithering of at least one of the sensors.

* * * * *